(12) United States Patent
Sahagan et al.

(10) Patent No.: US 6,417,229 B1
(45) Date of Patent: Jul. 9, 2002

(54) α-SULFONYLAMINO HYDROXAMIC ACID INHIBITORS OF MATRIX METALLOPROTEINASES FOR THE TREATMENT OF PERIPHERAL OR CENTRAL NERVOUS SYSTEM DISORDERS

(75) Inventors: Barbara G. Sahagan, Mystic; Anabella Villalobos, Niantic, both of CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/671,435

(22) Filed: Sep. 27, 2000

Related U.S. Application Data

(60) Provisional application No. 60/157,083, filed on Oct. 1, 1999.

(51) Int. Cl.[7] ............ A61K 31/215; A61K 31/445; A61K 31/395; A61K 31/295; A61K 31/405
(52) U.S. Cl. .......... 514/530; 514/330; 514/210; 514/562; 514/329; 514/459; 514/248; 514/408; 514/231.2; 514/415
(58) Field of Search ................ 514/530, 330, 514/210, 562, 329, 459, 248, 408, 231.2, 415

(56) References Cited

U.S. PATENT DOCUMENTS

| 5,817,822 A | 10/1998 | Nantermet et al. |
| 5,863,949 A | 1/1999 | Robinson et al. |
| 6,214,872 B1 * | 4/2001 | Robinson ............ 514/530 |
| 6,303,636 B1 | 10/2001 | Robinson et al. ....... 514/330 |

FOREIGN PATENT DOCUMENTS

| EP | 0895988 | | 2/1999 | |
| WO | 9627583 | | 9/1996 | |
| WO | WO 96/27583 | * | 9/1996 | ......... A61K/31/535 |
| WO | 9640101 | | 12/1996 | |
| WO | 9833768 | | 8/1998 | |
| WO | 9907675 | | 2/1999 | |
| WO | WO 99/07675 | * | 2/1999 | ......... A61K/31/19 |
| WO | 9952889 | | 10/1999 | |

* cited by examiner

*Primary Examiner*—Theodore J. Criares
(74) *Attorney, Agent, or Firm*—Peter C. Richardson; Paul H. Ginsburg; Jeffrey N. Myers

(57) ABSTRACT

The present invention relates to a method of using a compound of the formula (I):

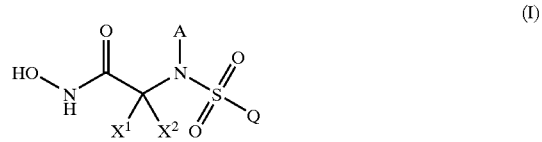

wherein A, $X^1$, $X^2$ and Q are as defined herein, a pharmaceutically acceptable salt thereof, or a pharmaceutical composition thereof, in the treatment of a disease, condition or disorder of the peripheral or central nervous system, including but not limited to Alzheimer's disease, stroke/cerebral ischemia, head trauma, spinal cord injury, multiple sclerosis, amyotrophic lateral sclerosis, Huntington's disease, Parkinson's disease, migraine, cerebral amyloid angiopathy, AIDS, age-related cognitive decline, mild cognitive impairment and prion diseases.

12 Claims, No Drawings

α-SULFONYLAMINO HYDROXAMIC ACID INHIBITORS OF MATRIX METALLOPROTEINASES FOR THE TREATMENT OF PERIPHERAL OR CENTRAL NERVOUS SYSTEM DISORDERS

This application claims the benefit of U.S. Ser. No. 60/157,083, filed Oct. 1, 1999.

BACKGROUND OF THE INVENTION

The present invention relates to new methods of using certain α-sulfonylamino hydroxamic acid inhibitors of matrix metalloproteinases in the treatment of diseases, conditions and disorders of the peripheral or central nervous system, including but not limited to Alzheimer's disease, stroke/cerebral ischemia, head trauma, spinal cord injury, multiple sclerosis, amyotrophic lateral sclerosis, Huntington's disease, Parkinson's disease, migraine, cerebral amyloid angiopathy, AIDS, age-related cognitive decline; mild cognitive impairment and prion diseases, and pharmaceutical compositions useful therefor.

The compounds of the present invention are inhibitors of zinc metalloendopeptidases, especially those belonging to the matrix metalloproteinase (also called MMP or matrixin) and reprolysin (also known as adamylsin) subfamilies of the metzincins (Rawlings, et al., *Methods in Enzymology*, 248, 183–228 (1995) and Stocker, et al., *Protein Science*, 4, 823–840 (1995)).

The MMP subfamily of enzymes, currently contains seventeen members (MMP-1, MMP-2, MMP-3, MMP-7, MMP-8, MMP-9, MMP-10, MMP-11, MMP-12, MMP-13, MMP-14, MMP-15, MMP-16, MMP-17, MMP-18, MMP-19, MMP-20). The MMP's are most well known for their role in regulating the turn-over of extracellular matrix (ECM) proteins and as such play important roles in normal physiological processes such as reproduction, development and differentiation.

In the central nervous system, the ECM not only serves structural and adhesive functions but also stimulates intracellular signaling pathways in response to association of the matrix with cell surface proteins. (Yong et al., *Trends in Neuroscience*, 21, 75–80 (1998)) Excessive expression of MMP's is believed to contribute to the pathogenesis of tissue destructive diseases such as arthritis, multiple sclerosis (MS) and cancer, conditions where inflammation and invasive processes play important roles. In Alzheimer's Disease (AD) and age-matched control samples, the expression of MMP's, particularly MMP-9 and MMP-2, is increased. The link between MMP's, AD and the ECM is supported by in vitro and in vivo evidence. In clinical samples taken from stroke, MS, amyotrophic lateral sclerosis (ALS) patients, increased expression of MMP's has also been documented. In AD, astrocytes produce inflammatory mediators and ECM proteins which surround neuritic plaques.

Like other members of the matrix metalloproteinase family, MMP-2 (72 kDa type IV collagenase or Gelatinase A) and MMP-9 (92 kDa type IV collagenase or Gelatinase B) are calcium-requiring, zinc containing endopeptidases which are secreted from cells in a latent pro-enzyme form (Yong et al., supra). These MMP's attack type IV collagen, laminen and fibronectin, the major components of the ECM surrounding cerebral blood vessels. Because of the dire consequences of inappropriate or unbalanced activity, they are tightly regulated by three independent mechanisms: proenzyme activation, gene transcription and inhibition by their endogenous inhibitor TIMP-1 (Borden and Heller, *Critical Reviews in Eurkaryotic Gene Expression*, 7, 159–178, (1997)). The expression of MMP-9 is induced by growth factors and inflammatory cytokines in an NF-κB and AP-1 dependent manner (Bond et al., *FEBS Letters*, 435, 29–34, (1998)). MMP-2 is generally constitutively expressed; however, its mRNA can be modulated by some of the same factors which modulate MMP-9 expression (Gottschall and Deb, *Neuroimmunomodulation*, 3, 69–75, (1996)).

Additionally, in AD hippocampus, MMP-9 protein is increased as much as four-fold (Backstrom et al., *J. Neurochemistry*, 58, 983–92 (1992)). The enzyme is predominantly found in its latent or proenzyme form in close proximity to extracellular amyloid plaques (Backstrom et al., *J. Neuroscience*, 16, 7910–19 (1996)). Similar observations were made in aged beagles. In amyloid-positive samples, statistically significant increases in latent MMP-9 were seen as compared with amyloid-negative samples (Lim et al., *J. Neurochemistry*, 68, 1606–11 (1997)).

The link between MMPs, AD and the ECM is supported by additional evidence (Perlmutter et al., *J. Neuroscience Res.*, 30, 673–81 (1991); Brandan and Inestrosa, *Gen. Pharmacology*, 24, 1063–8 (1993); Eikelenboom et al., *Virchows Archiv*, 424, 421–7 (1994); Luckenbill-Edds, *Brain Res. Revs.*, 23, 1–27 (1997)). Laminin is induced by brain injury and co-localizes with amyloid deposits in AD. In AD tissue, native human laminin was localized in large punctate, extracellular deposits which co-localize with plaques. Antibodies to the neurite-outgrowth promoting domains of laminin B2 or A chains localize to glia or capillary basement membranes, respectively. In control brains, laminin immunoreactivity is only found in capillaries (Murtomaki et al., *J. Neuroscience Res.*, 32, 261–73 (1993)). In a murine model of neurodegeneration (Chen and Strickland, *Cell*, 91, 917–25 (1997)), kainic acid challenged neurons secrete tPA. This initiates a cascade of proteolytic events beginning with conversion of plasminogen to plasmin and ending with degradation of laminin and subsequent death of neurons. Plasmin is a known activator of MMP-9 which could be part of this proteolytic cascade resulting in the eventual destruction of neurons.

In PC12 cells, laminin or specific laminin peptides are capable to stimulating MMP secretion and this mechanism is linked to laminin-mediated neurite outgrowth (Weeks et al., *Exp. Cell Res.*, 243, 375–82 (1998)). There has been a suggestion that these specific laminin sites may only be exposed in the basement membrane as observed in AD (Kibby et al., *Proc. Nat. Acad. Sci.*, 90, 10150–3 (1993)). Further deposition of Aβ could be nucleated by these laminin fragments which are found in neuritic plaques. Therefore, interfering with degradation of laminin could have the outcome of preserving the ECM, enhancing neuronal survival, and eliminating at least one protein which may act as a seed for nucleation of Aβ.

Elevated expression of MMP-9 and MMP-2 has also been documented in stroke, MS and ALS. After focal ischemia in humans, MMP-9 is markedly elevated in the infarcted tissue at two days post-infarction and remained elevated for months. Increases in MMP-2 were subtle at 2–5 days and like MMP-9, remained marked and significant for months (Clark et al., *Neuroscience Letters*, 238, 53–6 (1997)). Analysis of brain and spinal cord samples from ALS patients identified major bands of enzyme activity as MMP-2 and MMP-9; MMP-2 in astrocytes and MMP-9 in pyramidal neurons of the motor cortex and motor neurons of the spinal cord. Increases in MMP-9 were observed in ALS frontal and occipital cortices and spinal cord versus control samples. The high level of MMP-9 and its possible release at the synapse may destroy the structural integrity of the surrounding matrix thereby contributing to the pathogenesis of ALS. (Lim et al., *J. Neurochemistry*, 67, 251–9 (1996)). MMP-9 is elevated in CSF of MS patients and is detected by immunochemistry in active and chronic lesions. In autopsied samples from normal brain, MMP-like immunoreactivity (MMP-1, -2, -3 and -9) is localized to microglia and astrocytes. In MS patient samples, MMP expression is up-regulated in these glial cells and also in perivascular macrophages that are present in active brain lesion. (Chandler et al., *J. Neuroimmunology*, 72, 155–61 (1997); Liedtke et al., *Annals of Neurology*, 44, 35–46 (1998).)

In addition to the foregoing, MMP's have been associated with neuronal degeneration in a number of animal models. These models can be used in an MMP inhibitor program to track inhibitor activity and predict pre-clinical efficacy. After focal ischemia in rats, MMP-9 was shown to increase in the infarcted area during the first day (Rosenberg et al., *J. Cerebral Blood Flow & Metabolism*, 16, 360–6, (1996)). MMP-2 remained the same until 5 days after injury when it increased significantly. This time course of induction is very similar to that seen by Clark et al, supra, in human clinical stroke samples. (Rosenberg and Navratil, *Neurology*, 48, 921–6 (1997)) have also shown that metalloproteinase inhibition blocks edema in intracerebral hemorrhage in the rat. A model of direct injection of MMP's into the rat brain also demonstrated neuronal loss after MMP-9 or -2, but not MMP-8, injection as well as the loss of GFAP and myelin immunoreactivity (Anthony et al., *J. Neuroimmunology*, 87, 62–72 (1998)).

MMP-9 was detected in the CSF of mice with Experimental Autoimmune Encephelomyelitis (EAE), an animal model for MS. A hydroxamate inhibitor of MMP, GM6001, was found to suppress the development of, or reverse established, EAE (Gijbels, *J. Clinical Invest.*, 94, 2177–82 (1994)). Based on this model, MMP inhibitors might act by preventing the influx of inflammatory cells across the basement membrane or ECM barrier that surrounds cerebral endothelium. Another hydroxamic acid-based compound which is a combined inhibitor of MMP and TNF-α processing/release, BB-1101 (Redford et al., *Brain*, 120, 1895–905 (1997)), attenuates Experimental Autoimmune Neuritis (EAN), a model of Guillain-Barre syndrome.

Lastly, in vitro experiments suggest a role for MMP's in the development or progression of neuritic plaques. Deb and Gottschall, *J. Neurochemistry*, 66, 1641–7 (1996)), demonstrated that Aβ induces MMP-9 and -2 expression in astrocyte and mixed hippocampal cultures. Further, MMP-9 induction by Aβ in rat microglia can be inhibited by the anti-inflammatory agents dexamethasone and indomethacin (Gottschall, *Neuroreport*, 7, 3077–80 (1996)). This is of particular importance when considered in conjunction with clinical data which suggests that administration of anti-inflammatory drugs may slow the progression of AD (Rogers et al., *Arzneimittelforschung*, 45, 439–42 (1995)).

Applicants now disclose a method of treatment of diseases, conditions or disorders of the peripheral and central nervous system, including but not limited to Alzheimer's disease, stroke/cerebral ischemia, head trauma, spinal cord injury, multiple sclerosis, amyotrophic lateral sclerosis, Huntington's disease, Parkinson's disease, migraine, cerebral amyloid angiopathy, AIDS, age-related cognitive decline; mild cognitive impairment and prion diseases, comprising the administration of small molecule inhibitors of MMP-9, MMP-2 or mixed MMP inhibitors which may reduce neuronal damage and limit neuroinflammation.

However, the diseases in which inhibition of MMP's will provide therapeutic benefit include but are not limited to: arthritis (including osteoarthritis and rheumatoid arthritis), inflammatory bowel disease, Crohn's disease, emphysema, acute respiratory distress syndrome, asthma chronic obstructive pulmonary disease, Alzheimer's disease, organ transplant toxicity; cachexia, allergic reactions, allergic contact hypersensitivity, cancer, tissue ulceration, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), congestive heart failure, myocardial infarction, stroke, cerebral ischemia, head trauma, spinal cord injury, neurodegenerative disorders (acute and chronic), inflammatory and autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, bums, diabetes, tumor invasion, tumor growth, tumor metastasis, corneal scarring, scleritis, AIDS, sepsis, septic shock and other diseases characterized by metalloproteinase or ADAM expression. This invention also relates to methods of using the hydroxamic acid compounds described herein in the treatment of the above-identified diseases, conditions and disorders in mammals, especially humans, and to the pharmaceutical compositions containing these compounds useful in such methods.

It is recognized that different combinations of MMP's are expressed in different pathological situations. As such inhibitors with specific selectivities for individual MMP's may be preferred for individual diseases.

SUMMARY OF THE INVENTION

The present invention relates to a method of treating a disease or disorder of the peripheral or central nervous system, including but not limited to Alzheimer's disease, stroke/cerebral ischemia, head trauma, spinal cord injury, multiple sclerosis, amyotrophic lateral sclerosis, Huntington's disease, Parkinson's disease, migraine, cerebral amyloid angiopathy, AIDS, age-related cognitive decline; mild cognitive impairment and prion diseases in a mammal, which comprises administering to said mammal a therapeutically effective amount of a compound of formula (I):

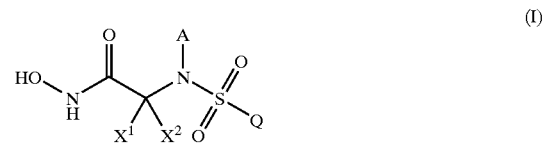

or the pharmaceutically acceptable salts thereof, wherein

A is H or —$(CH_2)_n$—(C=O)—Z; where n is 0 to 6; and Z is hydroxy, ($C_1$–$C_6$)alkoxy or $NR^1R^2$ wherein $R^1$ and $R^2$ are each independently selected from the group consisting of hydrogen, ($C_1$–$C_6$)alkyl, piperidyl, ($C_1$–$C_6$)alkylpiperidyl, ($C_6$–$C_{10}$)arylpiperidyl, ($C_2$–$C_9$)heteroarylpiperidyl, ($C_6$–$C_{10}$)aryl($C_1$–$C_6$)alkylpiperidyl, ($C_2$–$C_9$)heteroaryl($C_1$–$C_6$)alkylpiperidyl, ($C_1$–$C_6$)acylpiperidyl, ($C_6$–$C_{10}$)aryl, ($C_2$–$C_9$)heteroaryl, ($C_6$–$C_{10}$)aryl($C_1$–$C_6$)alkyl, $(C_2-C_9)$heteroaryl$(C_1-C_6)$alkyl, $(C_6-C_{10})$aryl$(C_6-C_{10})$aryl, $(C_6-C_{10})$aryl$(C_6-C_{10})$aryl$(C_1-C_6)$alkyl, $(C_3-C_6)$cycloalkyl, $(C_3-C_6)$cycloalkyl$(C_1-C_6)$alkyl, $R^5(C_2-C_6)$alkyl, $(C_1-C_5)$alkyl$(CHR^3)(C_1-C_6)$alkyl wherein $R^3$ is hydroxy, $(C_1-C_6)$acyloxy, $(C_1-C_6)$alkoxy, piperazino, $(C_1-C_6)$acylamino, $(C_1-C_6)$alkylthio, $(C_6-C_{10})$arylthio, $(C_1-C_6)$alkylsulfinyl, $(C_6-C_{10})$arylsulfinyl, $(C_1-C_6)$alkylsulfoxyl, $(C_6-C_{10})$arylsulfoxyl, amino, $(C_1-C_6)$alkylamino, $((C_1-C_6)$alkyl$)_2$ amino, $(C_1-C_6)$acylpiperazino, $(C_1-C_6)$alkylpiperazino, $(C_6-C_{10})$aryl$(C_1-C_6)$alkylpiperazino, $(C_2-C_9)$heteroaryl$(C_1-C_6)$alkylpiperazino, morpholino, thiomorpholino, piperidino or pyrrolidino; $R^4(C_1-C_6)$alkyl, $(C_1-C_5)$alkyl$(CHR^4)(C_1-C_6)$alkyl wherein $R^4$ is piperidyl, $(C_1-C_6)$alkylpiperidyl, $(C_6-C_{10})$arylpiperidyl, $(C_6-C_{10})$aryl$(C_1-C_6)$alkylpiperidyl, $(C_2-C_9)$heteroarylpiperidyl or $(C_2-C_9)$heteroaryl$(C_1-C_6)$alkylpiperidyl; and $CH(R^5)COR^6$ wherein $R^5$ is hydrogen, $(C_1-C_6)$alkyl, $(C_6-C_{10})$aryl$(C_1-C_6)$alkyl, $(C_2-C_9)$heteroaryl$(C_1-C_6)$alkyl, $(C_1-C_6)$alkylthio$(C_1-C_6)$alkyl, $(C_6-C_{10})$arylthio$(C_1-C_6)$alkyl, $(C_1-C_6)$alkylsulfinyl$(C_1-C_6)$alkyl, $(C_6-C_{10})$arylsulfinyl$(C_1-C_6)$alkyl, $(C_1-C_6)$alkylsulfonyl$(C_1-C_6)$alkyl, $(C_6-C_{10})$arylsulfonyl$(C_1-C_6)$alkyl, hydroxy$(Cl-C_6)$alkyl, amino$(C_1-C_6)$alkyl, $(C_1-C_6)$alkylamino$(C_1-C_6)$alkyl, $((C_1-C_6)$alkylamino$)_2(C_1-C_6)$alkyl, $R^7R^8NCO(C_1-C_6)$alkyl or $R^7OCO(C_1-C_6)$alkyl wherein $R^7$ and $R^8$ are each independently selected from the group consisting of hydrogen, $(C_1-C_6)$alkyl, $(C_6-C_{10})$aryl$(C_1-C_6)$alkyl and $(C_2-C_9)$heteroaryl$(C_1-C_6)$alkyl; and $R^6$ is $R^9O$ or $R^9R^{10}N$ wherein $R^9$ and $R^{10}$ are each independently selected from the group consisting of hydrogen, $(C_1-C_6)$alkyl, $(C_6-C_{10})$aryl$(C_1-C_6)$alkyl and $(C_2-C_9)$heteroaryl$(C_1-C_6)$alkyl;

or $R^1$ and $R^2$, or $R^7$ and $R^8$, or $R^9$ and $R^{10}$ may be taken together to form an azetidinyl, pyrrolidinyl, morpholinyl, thiomorpholinyl, indolinyl, isoindolinyl, tetrahydroquinolinyl, tetrahydroisoquinolinyl, $(C_1-C_6)$acylpiperazinyl, $(C_1-C_6)$alkylpiperazinyl, $(C_6-C_{10})$arylpiperazinyl, $(C_2-C_9)$heteroarylpiperazinyl or a bridged diazabicycloalkyl ring selected from the group consisting of:

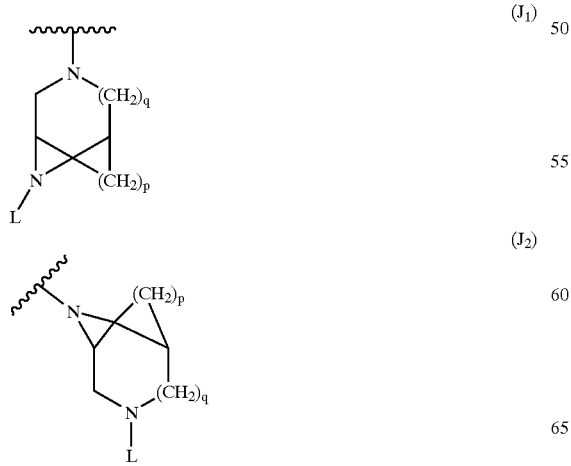

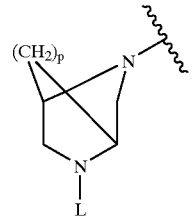

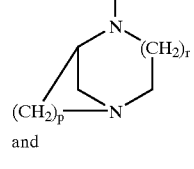

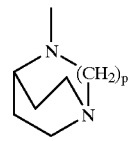

wherein p is 1, 2 or 3;
q is 1 or 2;
r is 0 or 1;
L is hydrogen, $(C_1-C_3)$alkyl or $(C_1-C_6)$acyl;
$X^1$ and $X^2$ are each independently selected from the group consisting of hydrogen, $(C_1-C_6)$alkyl, trifluoromethyl, trifluoromethyl$(C_1-C_6)$alkyl, $(C_1-C_6)$alkyl (difluoromethylene), $(C_1-C_3)$alkyl(difluoromethylene)$(C_1-C_3)$alkyl, $(C_6-C_{10})$aryl, $(C_2-C_9)$heteroaryl, $(C_6-C_{10})$aryl$(C_1-C_6)$alkyl, $(C_2-C_9)$heteroaryl$(C_1-C_6)$alkyl, $(C_6-C_{10})$aryl$(C_6-C_{10})$aryl, $(C_6-C_{10})$aryl$(C_6-C_{10})$aryl$(C_1-C_6)$alkyl, $(C_3-C_6)$cycloalkyl, $(C_3-C_6)$cycloalkyl$(C_1-C_6)$alkyl, hydroxy$(C_1-C_6)$alkyl, $(C_1-C_6)$acyloxy$(C_1-C_6)$alkyl, $(C_1-C_6)$alkoxy$(C_1-C_6)$alkyl, piperazinyl$(C_1-C_6)$alkyl, $(C_1-C_6)$acylamino$(C_1-C_6)$alkyl, piperidyl, $(C_1-C_6)$alkylpiperidyl, $(C_6-C_{10})$aryl$(C_1-C_6)$alkoxy$(C_1-C_6)$alkyl, $(C_2-C_9)$heteroaryl$(C_1-C_6)$alkoxy$(C_1-C_6)$alkyl, $(C_1-C_6)$alkylthio$(C_1-C_6)$alkyl, $(C_6-C_{10})$arylthio$(C_1-C_6)$alkyl, $(C_1-C_6)$alkylsulfinyl$(C_1-C_6)$alkyl, $(C_6-C_{10})$arylsulfinyl$(C_1-C_6)$alkyl, $(C_1-C_6)$alkylsulfonyl$(C_1-C_6)$alkyl, $(C_6-C_{10})$arylsulfonyl$(C_1-C_6)$alkyl, amino$(C_1-C_6)$alkyl, $(C_1-C_6)$alkylamino$(C_1-C_6)$alkyl, $((C_1-C_6)$alkylamino$)_2(C_1-C_6)$alkyl, $R^{11}CO(C_1-C_6)$alkyl wherein $R^{11}$ is $R^{12}O$ or $R^{12}R^{13}N$ wherein $R^{12}$ and $R^{13}$ are each independently selected from the group consisting of hydrogen, $(C_1-C_6)$alkyl, $(C_6-C_{10})$aryl$(C_1-C_6)$alkyl or $(C_2-C_9)$heteroaryl$(C_1-C_6)$alkyl; and $R^{14}(C_1-C_6)$alkyl wherein $R^{14}$ is $(C_1-C_6)$acylpiperazino, $(C_6-C_{10})$arylpiperazino, $(C_2-C_9)$heteroarylpiperazino, $(C_1-C_6)$alkylpiperazino, $(C_6-C_{10})$aryl$(C_1-C_6)$alkylpiperazino, $(C_2-C_9)$heteroaryl$(C_1-C_6)$alkylpiperazino, morpholino, thiomorpholino, piperidino, pyrrolidino, piperidyl, $(C_1-C_6)$alkylpiperidyl, $(C_6-C_{10})$arylpiperidyl, $(C_2-C_9)$heteroarylpiperidyl, $(C_6-C_{10})$aryl$(C_1-C_6)$alkylpiperidyl, $(C_2-C_9)$heteroaryl$(C_1-C_6)$alkylpiperidyl or $(C_1-C_6)$acylpiperidyl;

or $X^1$ and $X^2$ may be taken together to form a $(C_3-C_6)$ cycloalkyl, a benzo-fused $(C_3-C_6)$cycloalkyl ring or a group of the formula $(J_7)$:

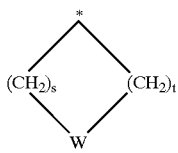

wherein the carbon atom bearing the asterisk is the carbon to which $X^1$ and $X^2$ are attached, s and t are each independently 1 or 2, and W is $CF_2$, O, S, $SO_2$ or $NR^{15}$, wherein $R^{15}$ is hydrogen, $(C_1-C_6)$alkyl, $(C_6-C_{10})$acyl, $(C_6-C_{10})$aryl, $(C_2-C_9)$heteroaryl, $(C_6-C_{10})$aryl$(C_1-C_6)$ alkyl, $(C_2-C_9)$heteroaryl$(C_1-C_6)$alkyl, $(C_1-C_6)$ alkylsulfonyl, $(C_6-C_{10})$arylsulfonyl or $(C_1-C_6)$alkyl $(C=O)-$;

Q is $(C_1-C_6)$alkyl, $(C_6-C_{10})$aryl, $(C_6-C_{10})$aryloxy $(C_6-C_{10})$aryl, $(C_6-C_{10})$aryl$(C_6-C_{10})$aryl, $(C_6-C_{10})$aryl $(C_6-C_{10})$aryl$(C_1-C_6)$alkyl, $(C_6-C_{10})$aryl$(C_2-C_9)$ heteroaryl, $(C_6-C_{10})$aryloxy$(C_2-C_9)$heteroaryl, $(C_2-C_9)$heteroaryl, $(C_2-C_9)$heteroaryl$(C_2-C_9)$ heteroaryl, $(C_2-C_9)$heteroaryl$(C_6-C_{10})$aryl, $(C_1-C_6)$ alkyl$(C_6-C_{10})$aryl, $(C_1-C_6)$alkoxy$(C_6-C_{10})$aryl, $((C_1-C_6)$alkoxy$)_2(C_6-C_{10})$aryl, $(C_6-C_{10})$aryl$(C_1-C_6)$ alkoxy$(C_6-C_{10})$aryl, $(C_6-C_{10})$aryl$(C_1-C_6)$alkoxy $(C_1-C_6)$alkyl, $(C_2-C_9)$heteroaryloxy$(C_6-C_{10})$aryl, $(C_1-C_6)$alkyl$(C_2-C_9)$heteroaryl, $(C_1-C_6)$alkoxy $(C_2-C_9)$heteroaryl, $((C_1-C_6)$alkoxy$)_2(C_2-C_9)$ heteroaryl, $(C_6-C_{10})$aryl$(C_1-C_6)$alkoxy$(C_2-C_9)$ heteroaryl, $(C_2-C_9)$heteroaryloxy$(C_2-C_9)$heteroaryl, $(C_6-C_{10})$aryloxy$(C_1-C_6)$alkyl, $(C_2-C_9)$heteroaryloxy $(C_1-C_6)$alkyl, $(C_1-C_6)$alkyl$(C_6-C_{10})$aryloxy$(C_6-C_{10})$ aryl, $(C_1-C_6)$alkyl$(C_2-C_9)$heteroaryloxy$(C_6-C_{10})$aryl, $(C_1-C_6)$alkyl$(C_6-C_{10})$aryloxy$(C_2-C_9)$heteroaryl, $(C_1-C_6)$alkoxy$(C_6-C_{10})$aryloxy$(C_6-C_{10})$aryl, $(C_1-C_6)$ alkoxy$(C_2-C_9)$heteroaryloxy$(C_6-C_{10})$aryl or $(C_1-C_6)$ alkoxy$(C_6-C_{10})$aryloxy$(C_2-C_9)$heteroaryl, wherein each of the foregoing aryl groups may be optionally substituted by fluoro, chloro, bromo, trifluoromethyl, trifluoromethoxy, difluoromethoxy, $(C_1-C_6)$alkyl, $(C_1-C_6)$alkoxy or perfluoro$(C_1-C_3)$alkyl;

with the proviso that when either $X^1$ or $X^2$ is $CH(R^5)$ $COR^6$ wherein $R^5$ and $R^6$ are as defined above, the other of $X^1$ or $X^2$ is hydrogen, $(C_1-C_6)$alkyl or benzyl.

One preferred embodiment of the present invention relates to a method of treating a disease, disorder or condition of the peripheral or central nervous system in a mammal, comprising the administration to a mammal a therapeutically effective amount of a compound of the formula (Ia):

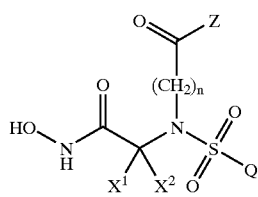

(Ia)

or a pharmaceutically acceptable salt thereof, wherein $X^1$, $X^2$, Q and Z are as defined above, and n is an integer from 1 to 6.

Preferred methods of the invention comprise the administration of a compound of formula (Ia) wherein n is 2. Other preferred methods of the invention comprise the administration of a compound of formula (Ia) wherein Q is 4-methoxyphenyl or 4-phenoxyphenyl, optionally substituted by fluoro, chloro, bromo, trifluoromethyl, trifluoromethoxy, difluoromethoxy, $(C_1-C_6)$alkyl, $(C_1-C_6)$ alkoxy or perfluoro$(C_1-C_3)$alkyl. Other preferred methods of the invention comprise the administration of a compound of formula (Ia) wherein either $X^1$ or $X^2$ is not hydrogen. Other preferred methods of the invention comprise the administration of a compound of formula (Ia) wherein Z is hydroxy, Q is 4-methoxyphenyl or 4-phenoxyphenyl, optionally substituted by fluoro, chloro, bromo, trifluoromethyl, trifluoromethoxy, difluoromethoxy, $(C_1-C_6)$ alkyl, $(C_1-C_6)$alkoxy or perfluoro$(C_1-C_3)$alkyl, and either $X^1$ or $X^2$ is not hydrogen.

Other preferred methods of the invention comprise the administration of a compound of formula (Ia) wherein Q is 4-methoxyphenyl or 4-phenoxyphenyl and $X^1$ and $X^2$ are taken together to form $(C_3-C_6)$cycloalkyl, oxacyclohexanyl, thiocyclohexanyl, indanyl or a group of the formula:

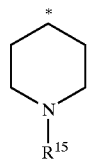

wherein the carbon bearing the asterisk is the carbon to which $X^1$ and $X^2$ are attached and $R^{15}$ is $(C_1-C_6)$acyl, $(C_1-C_6)$alkyl, $(C_6-C_{10})$aryl$(C_1-C_6)$alkyl, $(C_2-C_9)$ heteroaryl$(C_1-C_6)$alkyl or $(C_1-C_6)$alkylsulfonyl.

A more preferred embodiment of the present invention relates to a method of treating a disease, condition or disorder of the peripheral or central nervous system in a mammal comprising the administration of a therapeutically effective amount of a compound of the formula (Ic):

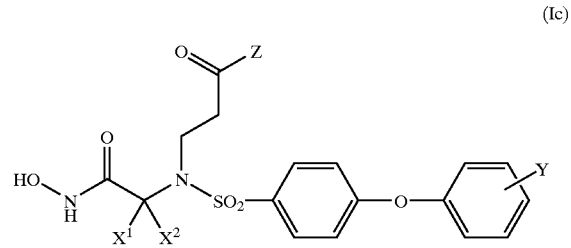

(Ic)

or the pharmaceutically acceptable salts thereof, wherein
$X^1$ is $(C_1-C_6)$alkyl;
$X^2$ is $(C_1-C_6)$alkyl; or
$X^1$ and $X^2$ taken together with the carbon atom to which they are attached form a ring selected from $(C_5-C_7)$ cycloalkyl, 4-tetrahydropyranyl and 4-piperidinyl;
Z is hydroxy or $(C_1-C_6)$alkoxy; and
Y is a substituent on any of the carbon atoms of the phenyl ring capable of supporting an additional bond, preferably from 1 to 2 substituents (more preferably one substituent, most preferably one substituent in the 4-position) on the phenyl ring, independently selected from hydrogen, fluoro, chloro, trifluoromethyl, $(C_1-C_6)$ alkoxy, trifluoromethoxy, difluoromethoxy and $(C_1-C_6)$alkyl.

The more preferred methods of the invention comprise the administration of a compound of formula (Ic) wherein Y is hydrogen, fluoro or chloro, preferably 4-fluoro or 4-chloro. Other more preferred methods comprise the administration of a compound of formula (Ic) wherein $X^1$ and $x^2$ taken together with the carbon atom to which they are attached form a cyclopentyl or 4-tetrahydropyranyl ring.

Other preferred methods of the invention comprise the administration of a compound of formula (Ic) wherein $X^1$ and $X^2$ are both methyl. Other preferred methods comprise the administration of a compound of formula (Ic) wherein Z is hydroxy.

Specifically, the most preferred methods of the invention comprise the administration of a compound of formula (Ic) selected from the group consisting of:

3-[[4-(4-fluorophenoxy)benzenesulfonyl]-(1-hydroxycarbamoylcyclopentyl)amino]-propionic acid ethyl ester;

3-[[4-(4-fluorophenoxy)benzenesulfonyl]-(1-hydroxycarbamoylcyclopentyl)amino]propionic acid;

3-[[4-(4-fluorophenoxy)benzenesulfonyl]-(1-hydroxycarbamoyl-1-methylethyl)amino]propionic acid ethyl ester;

3-[[4-(4-fluorophenoxy)benzenesulfonyl]-(1-hydroxycarbamoyl-1-methylethyl)amino]propionic acid;

3-[[4-(4-fluorophenoxy)benzenesulfonyl]-(4-hydroxycarbamoyltetrahydropyran-4-yl)-amino] propionic acid;

3-[[4-(4-fluorophenoxy)benzenesulfonyl]-(4-hydroxycarbamoyltetrahydropyran-4-yl)-amino] propionic acid ethyl ester;

3-[[4-(4-chlorophenoxy)benzenesulfonyl]-(4-hydroxycarbamoyltetrahydropyran-4-yl)-amino] propionic acid;

3-[[4-(4-chlorophenoxy)benzenesulfonyl]-(4-hydroxycarbamoyltetrahydropyran-4-yl)-amino] propionic acid ethyl ester;

3-[(4-hydroxycarbamoyltetrahydropyran-4-yl)-(4-phenoxybenzenesulfonyl)amino]-propionic acid;

3-[(4-hydroxycarbamoyltetrahydropyran-4-yl)-(4-phenoxybenzenesulfonyl)amino]-propionic acid ethyl ester;

3-[[4-(4-fluorophenoxy)benzenesulfonyl]-(4-hydroxycarbamoylpiperidin-4-yl)-amino]propionic acid ethyl ester;

3-[[4-(4-chlorophenoxy)benzenesulfonyl]-(1-hydroxycarbamoyl-1-methylethyl)amino]-propionic acid;

3-[[4-(4-chlorophenoxy)benzenesulfonyl]-(1-hydroxycarbamoyl-1-methylethyl)amino]-propionic acid ethyl ester;

3-[[4-(4-fluorophenoxy)benzenesulfonyl]-(1-hydroxycarbamoylcyclohexyl)amino]-propionic acid;

3-[(1-hydroxycarbamoylcyclopentyl)-(4-phenoxybenzenesulfonyl)amino]propionic acid;

3-[[4-(4-chlorophenoxy)benzenesulfonyl]-(1-hydroxycarbamoylcyclopentyl)amino]-propionic acid and pharmaceutically acceptable salts thereof.

The methods of the invention also encompass methods of treating or preventing comprising administering a prodrug of a compound of formula (I). A compound of formula (I) having a free amino, amido, hydroxy or carboxylic acid group can be converted into a prodrug. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of formula (I). The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Prodrugs also include compounds wherein carbonates, carbamates, amides and alkyl esters which are covalently bonded to the above substituents of formula (I) through the carbonyl carbon prodrug sidechain. Prodrugs also include compounds of formula (I) in which the hydroxamic acid and carbonyl moiety when taken together, for example, form a group of the formula (Id):

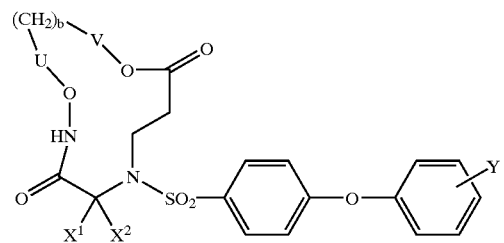

wherein $X^1$, $X^2$ and Y are as defined above and U and V are independently carbonyl, methylene, $SO_2$ or $SO_3$, and b is an integer from one to three wherein each methylene group is optionally substituted with hydroxy.

In addition to the foregoing preferred methods, further preferred embodiments of the present invention relates to a method of treatment of a condition, disease or disorder of the peripheral or central nervous system in a mammal comprising the administration of a compound of the formula (Ib):

(Ib)

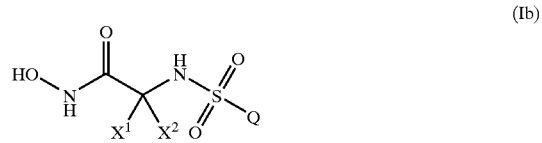

wherein $X^1$, $X^2$ and Q are as defined above.

Other preferred methods comprise the administration of a compound of formula (Ib) wherein $X^1$ and $x^2$ are taken together to form a $(C_3-C_6)$cycloalkyl or benzo-fused $(C_3-C_6)$cycloalkyl ring or a group of formula $J_7$:

($J_7$)

wherein the carbon atom bearing the asterisk is the carbon to which $X^1$ and $X^2$ are attached, s and t are independently 1 or 2; W is $CF_2$, S, O or $NR^{16}$ and $R^{16}$ is hydrogen, $(C_1-C_6)$alkyl, $(C_6-C_{10})$aryl, $(C_2-C_9)$ heteroaryl, $(C_6-C_{10})$aryl$(C_1-C_6)$alkyl, $(C_2-C_9)$ heteroaryl$(C_1-C_6)$alkyl, $(C_1-C_6)$alkylsulfonyl, $(C_6-C_{10})$arylsulfonyl or acyl.

Other preferred methods comprise the administration of a compound of formula (Ib) wherein $X^1$ and $X^2$ are taken together to form a ($C_3$–$C_6$)cycloalkyl or benzo-fused ($C_3$–$C_6$)cycloalkyl ring. Other preferred methods comprise the administration of a compound of formula (Ib) wherein Q is ($C_6$–$C_{10}$)aryl, ($C_6$–$C_{10}$)aryl($C_6$–$C_{10}$)aryl, ($C_6$–$C_{10}$)aryloxy($C_6$–$C_{10}$)aryl, ($C_6$–$C_{10}$)aryloxy($C_2$–$C_9$)heteroaryl, ($C_2$–$C_9$)heteroaryl, ($C_2$–$C_9$)heteroaryl($C_2$–$C_9$)heteroaryl, ($C_6$–$C_{10}$)aryl($C_2$–$C_9$)heteroaryl, ($C_2$–$C_9$)heteroaryl($C_6$–$C_{10}$)aryl or ($C_2$–$C_9$)heteroaryloxy($C_6$–$C_{10}$)aryl. Other preferred methods comprise the administration of a compound of formula (Ib) wherein Q is ($C_6$–$C_{10}$)aryloxy($C_6$–$C_{10}$)aryl. Other preferred methods comprise the administration of a compound of formula (Ib) wherein $X^1$ and $X^2$ are each independently ($C_1$–$C_6$)alkyl.

Other more preferred methods comprise the administration of a compound of formula (Ib) wherein $X^1$ and $X^2$ are taken together to form a ($C_3$–$C_6$)cycloalkyl or benzo-fused ($C_3$–$C_6$)cycloalkyl ring or a group of the formula ($J_7$):

($J_7$)

wherein the carbon atom bearing the asterisk is the carbon to which $X^1$ and $X^2$ are attached, s and t are independently 1 or 2 and $Q^9$ is $CF_2$, S, O or $NR^{16}$ wherein $R^{16}$ is hydrogen, ($C_1$–$C_6$)alkyl, ($C_6$–$C_{10}$)aryl, ($C_2$–$C_9$) heteroaryl, ($C_6$–$C_{10}$)aryl($C_1$–$C_6$)alkyl, ($C_2$–$C_9$) heteroaryl($C_1$–$C_6$)alkyl, ($C_1$–$C_6$)alkylsulfonyl, ($C_6$–$C_{10}$)arylsulfonyl or acyl; and Q is ($C_6$–$C_{10}$)aryl, ($C_6$–$C_{10}$)aryl($C_6$–$C_{10}$)aryl, ($C_6$–$C_{10}$)aryloxy($C_6$–$C_{10}$) aryl, ($C_6$–$C_{10}$)aryloxy-($C_2$–$C_9$)heteroaryl, ($C_2$–$C_9$) heteroaryl, ($C_2$–$C_9$)heteroaryl($C_2$–$C_9$)heteroaryl, ($C_6$–$C_{10}$)aryl($C_2$–$C_9$)heteroaryl, ($C_2$–$C_9$)heteroaryl ($C_6$–$C_{10}$)aryl or ($C_2$–$C_9$)heteroaryloxy($C_6$–$C_{10}$)aryl.

More preferred methods comprise the administration of a compound of formula (Ib) wherein $X^1$ and $X^2$ are taken together to form a ($C_3$–$C_6$)cycloalkyl or benzo-fused ($C_3$–$C_6$)cycloalkyl ring; and Q is ($C_6$–$C_{10}$)aryl, ($C_6$–$C_{10}$) aryl($C_6$–$C_{10}$)aryl, ($C_6$–$C_{10}$)aryloxy($C_6$–$C_{10}$)aryl, ($C_6$–$C_{10}$) aryloxy($C_2$–$C_9$)heteroaryl, ($C_2$–$C_9$)heteroaryl, ($C_2$–$C_9$) heteroaryl($C_2$–$C_9$)heteroaryl, ($C_6$–$C_{10}$)aryl($C_2$–$C_9$) heteroaryl, ($C_2$–$C_9$)heteroaryl($C_6$–$C_{10}$)aryl or ($C_2$–$C_9$) heteroaryloxy($C_6$–$C_{10}$)aryl.

More preferred methods comprise the administration of a compound of formula (Ib) wherein $X^1$ and $X^2$ are each independently ($C_1$–$C_6$)alkyl; and Q is ($C_6$–$C_{10}$)aryl, ($C_6$–$C_{10}$)aryl($C_6$–$C_{10}$)aryl, ($C_6$–$C_{10}$)aryloxy($C_6$–$C_{10}$)aryl, ($C_6$–$C_{10}$)heteroaryl, ($C_2$–$C_9$)heteroaryl, ($C_2$–$C_9$)heteroaryl ($C_2$–$C_9$)heteroaryl, ($C_6$–$C_{10}$)aryl($C_2$–$C_9$)heyeroaryl, ($C_2$–$C_9$)heteroaryl($C_6$–$C_{10}$)aryl or ($C_2$–$C_9$)heteroaryloxy ($C_6$–$C_{10}$)aryl. More preferred methods utilize compounds of formula (Ib) wherein $X^1$ and $X^2$ are each independently ($C_1$–$C_6$)alkyl; and Q is ($C_6$–$C_{10}$)aryloxy($C_6$–$C_{10}$)aryl.

Further, in addition to the methods stated above, other preferred methods comprise the administration of a compound of formula (Ia), supra, wherein n is 1 and either of $R^1$ or $R^2$ is hydrogen. Other preferred methods comprise the administration of a compound of formula (Ia) wherein Z is alkoxy, Q is 4-methoxyphenyl or 4-phenoxyphenyl and either $X^1$ or $X^2$ is not hydrogen. More preferred methods comprise the administration of a compound of formula (Ia) wherein n is 2, Q is 4-methoxyphenyl or 4-phenoxyphenyl, $R^1$ and $R^2$ taken together to form piperazinyl, ($C_1$–$C_6$) alkylpiperazinyl, ($C_6$–$C_{10}$)aryl piperazinyl or ($C_2$–$C_9$) heteroaryl($C_1$–$C_6$)alkylpiperazinyl, and either $X^1$ or $X^2$ is not hydrogen or both $X^1$ and $X^2$ are not hydrogen. More preferred methods comprise the administration of a compound of formula (Ia) wherein n is 2, Q is 4-methoxyphenyl or 4-phenoxyphenyl, $R^1$ is hydrogen or ($C_1$–$C_6$)alkyl, $R^2$ is 2-pyridylmethyl, 3-pyridylmethyl or 4-pyridylmethyl, and either $X^1$ or $X^2$ is not hydrogen or both $X^1$ and $X^2$ are not hydrogen. More preferred methods comprise the administration of a compound of formula (Ia) wherein n is 1, Q is 4-methoxyphenyl or 4-phenoxyphenyl, $R^1$ is hydrogen, $R^2$ is 2-pyridylmethyl, 3-pyridylmethyl or 4-pyridylmethyl, and either $X^1$ or $X^2$ is not hydrogen or both $X^1$ and $X^2$ are not hydrogen. More preferred methods comprise the administration of a compound of formula (Ia) wherein n is 2, Q is 4-methyoxyphenyl, $R^1$ is hydrogen or ($C_1$–$C_6$)alkyl and $R^2$ is $R^3$($C_2$–$C_6$)alkyl wherein $R^3$ is morpholino, thiomorpholino, piperidino, pyrrolidino, ($C_1$–$C_6$) acylpiperazino, ($C_1$–$C_6$)akylpiperazino, ($C_6$–$C_{10}$) arylpiperazino, ($C_2$–$C_9$)heteroarylpiperazino, ($C_6$–$C_{10}$)aryl ($C_1$–$C_6$)alkylpiperazino or ($C_2$–$C_9$)heteroaryl($C_1$–$C_6$) alkylpiperazino and either $X^1$ or $X^2$ is not hydrogen or both $X^1$ and $X^2$ are not hydrogen. More preferred methods comprise the administration of a compound of formula (Ia) wherein n is 1, Q is 4-methoxyphenyl or 4-phenoxyphenyl, $R^1$ is hydrogen, $R^2$ is $R^3$($C_2$–$C_6$)alkyl wherein $R^3$ is morpholino, thiomorpholino, piperidino, pyrrolidino, ($C_1$–$C_6$)acylpiperazino, ($C_1$–$C_6$)akylpiperazino, ($C_6$–$C_{10}$) arylpiperazino, ($C_2$–$C_9$)heteroarylpiperazino, ($C_6$–$C_{10}$)aryl ($C_1$–$C_6$)alkylpiperazino or ($C_2$–$C_9$)heteroaryl($C_1$–$C_6$) alkylpiperazino, and either $X^1$ or $X^2$ is not hydrogen or both $X^1$ and $X^2$ are not hydrogen.

In the foregoing discussion, the term "alkyl", as used herein, unless otherwise indicated, includes saturated monovalent hydrocarbon radicals having straight, branched or cyclic moieties or combinations thereof.

The term "alkoxy", as used herein, includes O-alkyl groups wherein "alkyl" is as defined above.

The term "aryl", as used herein, unless otherwise indicated, includes an organic radical derived from an aromatic hydrocarbon by removal of one hydrogen, such as phenyl or naphthyl, optionally substituted by 1 to 3 substituents selected from the group consisting of fluoro, chloro, bromo, perfluoro($C_1$–$C_6$)alkyl (including trifluoromethyl), ($C_1$–$C_6$)alkoxy, ($C_6$–$C_{10}$)aryloxy, perfluoro($C_1$–$C_3$)alkoxy (including trifluoromethoxy and difluoromethoxy) and ($C_1$–$C_6$)alkyl.

The term "heteroaryl", as used herein, unless otherwise indicated, includes an organic radical derived from an aromatic heterocyclic compound by removal of one hydrogen, such as pyridyl, furyl, pyrrolyl, thienyl, isothiazolyl, imidazolyl, benzimidazolyl, tetrazolyl, pyrazinyl, pyrimidyl, quinolyl, isoquinolyl, benzofuryl, isobenzofuryl, benzothienyl, pyrazolyl, indolyl, isoindolyl, purinyl, carbazolyl, isoxazolyl, thiazolyl, oxazolyl, benzthiazolyl or benzoxazolyl, optionally substituted by 1 to 2 substituents selected from the group consisting of fluoro, chloro, trifluoromethyl, ($C_1$–$C_6$)alkoxy, ($C_6$–$C_{10}$)aryloxy, trifluoromethoxy, difluoromethoxy and ($C_1$–$C_6$)alkyl. Preferred heteroaryl groups include pyridyl, furyl, thienyl, isothiazolyl, pyrazinyl, pyrimidyl, pyrazolyl, isoxazolyl, thiazolyl or oxazolyl. Most preferred heteroaryl groups include pyridyl, furyl or thienyl.

The term "acyl", as used herein, unless otherwise indicated, includes a radical of the general formula RCO wherein R is alkyl, alkoxy, aryl, arylalkyl or arylalkyloxy and the terms "alkyl" or "aryl" are as defined above.

The term "acyloxy", as used herein, includes O-acyl groups wherein "acyl" is defined above.

The term "treating" refers to, and includes, reversing, alleviating, inhibiting the progress of, or preventing a disease, disorder or condition, or one or more symptoms thereof; and "treatment" and "therapeutically" refer to the act of treating, as defined above.

A "therapeutically effective amount" is any amount of any of the compounds utilized in the course of practicing the invention provided herein that is sufficient to reverse, alleviate, inhibit the progress of, or prevent a disease, disorder or condition, or one or more symptoms thereof.

The methods of the invention comprise the administration of a compound of formula (I) which may have chiral centers and therefore exist in different enantiomeric forms. This invention relates to all optical isomers, tautomers and stereoisomers of the compounds of formula (I) and mixtures thereof.

The present invention also relates to a method comprising the administration of a pharmaceutically acceptable acid addition salt of a compound of the formula (I). The possible acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate (i.e., 1,1'-methylene-bis-(2-hydroxy-3-naphthoate)) salts.

The invention also relates to a method comprising the administration of a base addition salt of a compound of formula (I). The chemical bases that may be used as reagents to prepare pharmaceutically acceptable base salts of those compounds of formula (I) that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The subject invention also relates to a method of treatment which relates to isotopically-labeled compounds, which are identical to those recited in formula (I), but for the fact that one or more atoms are replaced by an atom having an atomic mass or mass number different from the atomic mass or mass number usually found in nature. Examples of isotopes that can be incorporated into compounds relating to the present invention include isotopes of hydrogen, carbon, nitrogen, oxygen, phosphorous, fluorine and chlorine, such as $^2H$, $^3H$, $^{13}C$, $^{14}C$, $^{15}N$, $^{15}O$, $^{17}O$, $^{31}P$, $^{32}P$, $^{35}S$, $^{18}F$, and $^{36}Cl$, respectively. Compounds relating to the present invention, prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances.

The present invention also relates to a pharmaceutical composition for the treatment of a disease, condition or disorder of the peripheral or central nervous system, wherein the disease, condition or disorder is Alzheimer's disease, stroke/cerebral ischemia, head trauma, spinal cord injury, multiple sclerosis, amyotrophic lateral sclerosis, Huntington's disease, Parkinson's disease, migraine, cerebral amyloid angiopathy, AIDS, age-related cognitive decline; mild cognitive impairment or a prion disease.

The present invention also relates to a pharmaceutical composition for treating of a disease, disorder or condition, wherein the disease, condition or disorder is arthritis (including osteoarthritis and rheumatoid arthritis), inflammatory bowel disease, Crohn's disease, emphysema, chronic obstructive pulmonary disease, Alzheimer's disease, organ transplant toxicity, cachexia, allergic reactions, allergic contact hypersensitivity, cancer, tissue ulceration, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), congestive heart failure, myocardial infarction, stroke, cerebral ischemia, head trauma, spinal cord injury, neurodegenerative disorders (acute and chronic), inflammatory and autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, tumor invasion, tumor growth, tumor metastasis, corneal scarring, scleritis, AIDS, sepsis, septic shock, other diseases characterized by metalloproteinase activity or other diseases characterized by mammalian reprolysin activity in a mammal, including a human, comprising an amount of a compound of formula (I) or a pharmaceutically acceptable salt thereof effective in such treatments and a pharmaceutically acceptable carrier.

This invention also encompasses pharmaceutical compositions containing a prodrug of a compound of the formula (I). This invention also encompasses methods of treating or preventing disorders that can be treated or prevented by the inhibition of matrix metalloproteinases or the inhibition of mammalian reprolysin comprising a administering prodrug of compounds of the formula (I). A compound of formula (I) having a free amino, amido, hydroxy or carboxylic group can be converted into a prodrug. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of formula (I). The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline, homocysteine, homoserine, omithine and methionine sulfone. Prodrugs also include compounds wherein carbonates, carbamates, amides and alkyl esters which are covalently bonded to the above substituents of formula I through the carbonyl carbon prodrug side chain.

One of ordinary skill in the art will appreciate that the methods of the invention are useful in treating a diverse array of diseases. One of ordinary skill in the art will also appreciate that when using the methods of the invention in the treatment of a specific disease that the methods of the invention may be combined with various existing therapeutic methods and agents used for that disease.

The present invention also relates to combination therapies using, or combination pharmaceutical compositions comprising, a compound of formula (I) and, e.g., a standard non-steroidal anti-inflammatory drug (NSAID'S), such as piroxicam, diclofenac, a propionic acid, such as naproxen, flubiprofen, fenoprofen, ketoprofen and ibuprofen, a fenamate, such as mefenamic acid, indomethacin, sulindac, apazone, a pyrazolone, such as phenylbutazone; a salicylate, such as aspirin; an analgesic or intraarticular therapy, such as a corticosteroid and a hyaluronic acid, such as hyalgan and synvisc; an immune suppressant, such as cyclosporin, interferon, etc., e.g., in organ transplant therapy; a TNF-α inhibitor agent, such as an anti-TNF monoclonal antibody, a TNF receptor immunoglobulin molecule (such as Enbrel®), low dose methotrexate, lefunimide, hydroxychloroquine, d-penicilamine, auranofin, parenteral gold, oral gold, etc.

The methods of present invention also relate to combination therapies using or combination pharmaceutical compositions comprising, a compound of formula (I) and, e.g., a CNS agent or agents, such as an antidepressant (e.g., sertraline, fluoxetine, paroxetine, etc.); an anti-Parkinsonian drug, such as deprenyl, L-dopa, requip, miratex, etc.; a MAOB inhibitor, such as selegine, rasagiline, etc.; a COMP inhibitor, such as tolcapone (i.e., Tasmar); an A-2 inhibitor; a dopamine reuptake inhibitor; an NMDA antagonist; a nicotine agonist; a dopamine agonist; an inhibitor of neuronal nitric oxide synthase; an anti-Alzheimer's drug; an acetylcholinesterase inhibitor, such as metrifonate, donepezil (i.e., Aricept), Exelon (i.e., ENA 713 or rivastigmine), etc.; tetrahydroaminoacridine (i.e., Tacrine, Cognex, or THA); a COX-1 or COX-2 inhibitor, such as celecoxib (i.e., Celebrex), rofecoxib (i.e., Vioxx), etc.; propentofylline; an anti-stroke medication; an NR2B selective antagonist; a glycine site antagonist; a neutrophil inhibitory factor (NIF), etc. The methods of the present invention further relate to combination therapies using, or combination pharmaceutical compositions comprising, a compound of formula (I) and, e.g., an estrogen; a selective estrogen modulator, such as estrogen, raloxifene, tamoxifene, droloxifene, lasofoxifene, etc. The methods of the present invention also relate to combination therapies using, or combination pharmaceutical compositions comprising, a compound of formula (I) and, e.g., an agent that results in reduction of Aβ1-40/1-42, such as an amyloid aggregation inhibitor, a secretase inhibitor, etc.

Further, the methods of present invention also relate to combination therapies using, or combination pharmaceutical compositions comprising, a compound of formula (I) and, e.g., an osteoporosis agents such as droloxifene or fosomax and immunosuppressant agents such as FK-506 and rapamycin. The methods of present invention also relate to combination therapies using, or combination pharmaceutical compositions comprising, a compound of formula (I) and, e.g., an anticancer agent; such as endostatin and angiostatin; a cytotoxic drug, such as adriamycin, daunomycin, cis-platinum, etoposide, taxol, taxotere or an alkaloid, such as vincristine; an antimetabolite, such as methotrexate; a cardiovascular agent, such as calcium channel blockers; a lipid lowering agent, such as a statin, a fibrate, a beta-blocker, an ACE inhibitor, an angiotensin-2 receptor antagonist or a platelet aggregation inhibitor. The methods of present invention also relate to combination therapies comprising the administration of compounds of formula (I) and another treatment, such as, e.g., fetal implant surgery treatment, gene therapy, etc.

DETAILED DESCRIPTION OF THE INVENTION

Matrix metalloproteinase inhibitors, including MMP-2 and MMP-9 selective inhibitors, utilized in accordance with the methods of the present invention, can be prepared according to methods well known to those of ordinary skill in the art. Specifically, methods for the preparation of the a-sulfonylamino hydroxamic acid matrix metalloproteinase inhibitors used. in the methods of the present invention have been described in PCT Publication WO 96/27583, published Mar. 7, 1996, filed as U.S. patent application Ser. No. 08/401,049 on Mar. 8, 1995; PCT Publication WO 98/33768, published Aug. 6, 1998, filed as U.S. patent application Ser. No. 09/355,163 on Jan. 12, 1998; and PCT Publication WO 99/07675, published Feb. 18, 1999, filed as U.S. patent application Ser. No. 60/055,207 on Aug. 8, 1997. The content of the foregoing U.S. patent applications are hereby incorporated in their entirety by reference. Isotopically labeled compounds of formula (I) of this invention and prodrugs thereof can generally be prepared by carrying out the procedures disclosed in the Schemes and/or in the Examples and Preparations of the foregoing incorporated applications, by substituting a readily available isotopically labeled reagent for a non-isotopically labeled reagent.

The following additional U.S. patent applications relating specifically to other matrix metalloproteinase inhibitors with broad activity and their methods of preparation are also hereby incorporated by reference: U.S. patent application Ser. No. 09/154,969, filed Sep. 17, 1998 which refers to non-selective cyclic aryl sulfonamino hydroxamic acids; U.S. patent application Ser. No. 08/855,023, filed May 13, 1997 which refers to cyclic imides as MMP inhibitors; U.S. patent application Ser. No. 08/881,092, filed Jul. 9, 1997, which refers to cyclic sulfone hydroxamic acids useful as MMP inhibitors; U.S. patent application Ser. No. 09/242,504, filed Jul. 25, 1997, which refers to aryl sulfonamino hydroxamic acids; U.S. patent application Ser. No. 08/892,417 filed Jul. 14, 1997 which refers to phosphanates that are useful as MMP inhibitors; U.S. patent application Ser. No. 09/125,055, filed Jan. 16, 1998, which refers to cyclic aryl sulfonamino hydroxamic acids useful in MMP inhibitors; U.S. patent application Ser. No. 09/341,226, filed Jan. 27, 1998, which refers to N-hydroxy-β-sulfonyl propionamides useful as MMP inhibitors; U.S. patent application Ser. No. 09/331,275, filed Dec. 18, 1997, which refers to cyclic sulfones as useful MMP inhibitors; U.S. patent application Ser. No. 09/233,883, filed Jan. 20, 1999; U.S. patent application Ser. No. 09/216,402, filed Dec. 18, 1998; U.S. patent application Ser. No. 09/130,922, filed Aug. 6, 1998; (U.S. patent application Ser. No. 09/290022, filed Apr. 9, 1999, U.S. patent application Ser. No. 09/287930, filed Apr. 7, 1999; and U.S. patent application Ser. No. 09/287,508, filed Apr. 7, 1999.

Further applications relating to matrix metalloproteinase inhibitor compounds hereby incorporated by reference are the following: PCT Application No. PCT/EP98/08565, filed Dec. 23, 1998; and PCT Application No. PCT/EP98/06640, filed Oct. 9, 1998.

The ability of matrix metalloproteinase inhibitors or their pharmaceutically acceptable salts (hereinafter also referred to as the inhibitors utilized in the present invention) to inhibit matrix metalloproteinases and a demonstration of their effectiveness for treating diseases of the peripheral and central nervous system is shown by the following in vitro assay tests.

In studying the regulation of genes in cytokine-stimulated human astrocytes, over-expression of one of the endogenous inhibitors of MMP, TIMP-1 (Tissue Inhibitor of Metalloproteinase 1) has been detected. In AD and age-matched controlled brains, increased expression of TIMP-1, MMP-2 and MMP-9 has been observed Increased expression of two of the MMP's known to be inhibited by TIMP-1, MMP-2 and MMP-9, has been demonstrated (See, Table 1). Brain tissue from the hippocampus and superior frontal gyrus (SFG) have been selected for analysis because they are severely affected by AD degeneration; cerebellum was studied because it is relatively unaffected by the disease process. It has been determined that the expression of MMP-2, MMP-9 and TIMP-1 are all increased in the hippocampus and SFG. MMP-2 and -9 are also up-regulated in the cerebellum but perhaps not to as great an extent.

TABLE 1

Ratio of mRNA Expression in AD v. Age-matched Control Brain Regions.

|  | Hippocampus Region | SFG Region | Cerebellum Region |
|---|---|---|---|
| MMP-2 | 2.5 (p = 0.002) | 2.4 (p = 0.006) | 1.5 (p = 0.033) |
| MMP-9 | 3.3 (p = 0.040) | 6.4 (p = 0.006) | 2.5 (p = 0.045) |
| TIMP-1 | 1.8 (p = 0.006) | 2.2 (p = 0.003) | 1.1 (p = 0.541) |

Biological Assay

The following assays may be used to identify matrix metalloproteinase inhibitors.

Inhibition of Human Collagenase (MMP-1)

Human recombinant collagenase is activated with trypsin using the following ratio: 10 μg trypsin per 100 μg of collagenase. The trypsin and collagenase are incubated at room temperature for 10 minutes then a five fold excess (50 μg/10 μg trypsin) of soybean trypsin inhibitor is added.

10 mM stock solutions of inhibitors are made up in dimethyl sulfoxide and then diluted using the following Scheme:

10 mM→120 μM→12 μM→1.2 μM→0.12 μM

Twenty-five microliters of each concentration is then added in triplicate to appropriate wells of a 96 well microfluor plate. The final concentration of inhibitor will be a 1:4 dilution after addition of enzyme and substrate. Positive controls (enzyme, no inhibitor) are set up in wells D1–D6 and blanks (no enzyme, no inhibitors) are set in wells D7–D12.

Collagenase is diluted to 240 ng/ml and 25 μl is then added to appropriate wells of the microfluor plate. Final concentration of collagenase in the assay is 60 ng/ml.

Substrate (DNP-Pro-Cha-Gly-Cys(Me)-His-Ala-Lys(NMA)-NH$_2$) is made as a 5 mM stock in dimethyl sulfoxide and then diluted to 20 μM in assay buffer. The assay is initiated by the addition of 50 μl substrate per well of the microfluor plate to give a final concentration of 10 μM.

Fluorescence readings (360 nM excitation, 460 nm emission) were taken at time 0 and then at 20 minute intervals. The assay is conducted at room temperature with a typical assay time of 3 hours.

Fluorescence vs time is then plotted for both the blank and collagenase containing samples (data from triplicate determinations is averaged). A time point that provides a good signal (the blank) and that is on a linear part of the curve (usually around 120 minutes) is chosen to determine IC$_{50}$ values. The zero time is used as a blank for each compound at each concentration and these values are subtracted from the 120 minute data. Data is plotted as inhibitor concentration vs % control (inhibitor fluorescence divided by fluorescence of collagenase alone ×100). IC$_{50}$'s are determined from the concentration of inhibitor that gives a signal that is 50% of the control.

If IC$_{50}$'s are reported to be <0.03 μM then the inhibitors are assayed at concentrations of 0.03 μM, 0.003 μM, 0.0003 μM and 0.00003 μM.

Inhibition of Gelatinase (MMP-2)

Inhibition of gelatinase activity is assayed using the MCA-Pro-Leu-Gly-Leu-Dpa-Ala-Arg-NH$_2$ substrate (10 μM) under the same conditions as inhibition of human collagenase (MMP-1).

72 kD gelatinase is activated with 1 mM APMA (p-aminophenyl mercuric acetate) for 16–18 hours at 4° C. and is diluted to give a final concentration in the assay of 25 ng/ml. Inhibitors are diluted as for inhibition of human collagenase (MMP-1) to give final concentrations in the assay of 30 μM, 3 μM, 0.3 1 μM and 0.03 μM. Each concentration is done in triplicate.

Fluorescence readings (320 nm excitation, 390 emission) are taken at time zero and then at 15 minutes intervals for 3 hours.

IC$_{50}$'s are determined as per inhibition of human collagenase (MMP-1). If IC$_{50}$'s are reported to be less than 0.03 μM, then the inhibitors are assayed at final concentrations of 0.03 μM, 0.003 μM, 0.0003 μM and 0.00003 μM.

Inhibition of Stromelysin Activity (MMP-3)

Inhibition of stromelysin activity is assayed using Mca-Arg-Pro-Lys-Pro-Val-Glu-Nva-Trp-Arg-Lys(Dnp)-NH$_2$ (3 μM) under conditions similar as in inhibition of human collagenase (MMP-1).

Human stromelysin is activated for 20–24 hours at 37° C. with 2 mM APMA (p-aminophenyl mercuric acetate) and is diluted to give a final concentration in the assay of 50 ng/ml. Inhibitors are diluted as for inhibition of human collagenase (MMP-1) to give final concentrations in the assay of 30 μM, 3 μM, 0.3 μM, and 0.03 μM. Each concentration is done in triplicate.

Fluorescence readings (320 nm excitation, 390 emission) are taken at time zero and then at 15 minute intervals for 3 hours.

IC$_{50}$'s are determined as per inhibition of human collagenase (MMP-1). If IC$_{50}$'s are reported to be less than 0.03 μM, then the inhibitors are assayed at final concentrations of 0.03 μM, 0.003 μM, 0.0003 μM, and 0.00003 μM.

Inhibition of Gelatinase (MMP-9)

Inhibition of gelatinase activity is assayed using the MCA-Pro-Leu-Gly-Leu-Dpa-Ala-Arg-NH$_2$ substrate (10 μM) under the same conditions as inhibition of human collagenase (MMP-1).

92 kD gelatinase is activated with 1.5 mM APMA (p-aminophenyl mercuric acetate) for 2 hours at 37° C. and is diluted to give a final concentration in the assay of 25 ng/ml. Inhibitors are diluted as for inhibition of human collagenase (MMP-1) to give final concentrations in the assay of 30 μM, 3 μM, 0.3 μM and 0.03 μM. Each concentration is done in triplicate.

Fluorescence readings (320 nm excitation, 390 emission) are taken at time zero and then at 15 minutes intervals for 3 hours.

IC$_{50}$'s are determined as per inhibition of human collagenase (MMP-1). If IC$_{50}$'s are reported to be less than 0.03 µM, then the inhibitors are assayed at final concentrations of 0.03 µM, 0.003 µM, 0.0003 µM and 0.00003 µM.

Inhibition of MMP-13

Human recombinant MMP-13 is activated with 2 mM APMA (p-aminophenyl mercuric acetate) for 1.5 hours, at 37° C. and is diluted to 240 µg/ml in assay buffer (50 mM Tris, pH 7.5, 200 mM sodium chloride, 5 mM calcium chloride, 20 µM zinc chloride, 0.02% brij). Twenty-five microliters of diluted enzyme is added per well of a 96 well microfluor plate. The enzyme is then diluted in a 1:4 ratio in the assay by the addition of inhibitor and substrate to give a final concentration in the assay of 60 µg/ml.

10 mM stock solutions of inhibitors are made up in dimethyl sulfoxide and then diluted in assay buffer as per the inhibitor dilution scheme for inhibition of human collagenase (MMP-1): Twenty-five microliters of each concentration is added in triplicate to the microfluor plate. The final concentrations in the assay are 30 µM, 3 µM, 0.3 µM, and 0.03 µM.

Substrate (Dnp-Pro-Cha-Gly-Cys(Me)-His-Ala-Lys (NMA)-NH$_2$) is prepared as for inhibition of human collagenase (MMP-1) and 50 µl is added to each well to give a final assay concentration of 10 µM. Fluorescence readings (360 nM excitation; 450 emission) are taken at time 0 and every 5 minutes for 1 hour.

Positive controls consist of enzyme and substrate with no inhibitor and blanks consist of substrate only.

IC$_{50}$'s are determined as per inhibition of human collagenase (MMP-1). If IC$_{50}$'s are reported to be less than 0.03 µM, inhibitors are then assayed at final concentrations of 0.03 µM, 0.003 µM, 0.0003 µM and 0.00003 µM.

Collagen film MMP-13 Assay

Rat type I collagen is radiolabeled with $^{14}$C acetic anhydride (T. E. Cawston and A. J. Barrett, *Anal. Biochem.*, 99, 340–345 (1979)) and used to prepare 96 well plates containing radiolabeled collagen films (Barbara Johnson-Wint, *Anal. Biochem.*, 104, 175–181 (1980)). When a solution containing collagenase is added to the well, the enzyme cleaves the insoluble collagen which unwinds and is thus solubilized. Collagenase activity is directly proportional to the amount of collagen solubilized, determined by the proportion of radioactivity released into the supernatant as measured in a standard scintillation counter. Collagenase inhibitors are, therefore, compounds which reduce the radioactive counts released with respect to the controls with no inhibitor present. One specific embodiment of this assay is described in detail below.

For determining the selectivity of compounds for MMP-13 versus MMP-1 using collagen as a substrate, the following procedure is used. Recombinant human proMMP-13 or proMMP-1 is activated according to the procedures outlined above. The activated MMP-13 or MMP-1 is diluted to 0.6 µg/ml with buffer (50 mM Tris pH 7.5, 150 mM NaCl, 10 mM CaCl$_2$, 1 µM ZnCl$_2$, 0.05% Brij-35, 0.02% sodium azide).

Stock solutions of test compound (10 mM) in dimethylsulfoxide are prepared. Dilutions of the test compounds in the Tris buffer, above, are made to 0.2, 2.0, 20, 200, 2000 and 20000 nM. 100 µl of appropriate drug dilution and 100 µl of diluted enzyme are pipetted into wells of a 96 well plate containing collagen films labeled with $^{14}$C-collagen. The final enzyme concentration is 0.3 µg/ml while the final drug concentration is 0.1, 1.0, 10, 100, 1000 nM. Each drug concentration and control is analyzed in triplicate. Triplicate controls are also run for the conditions in which no enzyme is present and for enzyme in the absence of any compound.

The plates are incubated at 37° C. for a time period such that around 30–50% of the available collagen is solubilized—determined by counting additional control wells at various time points. In most cases around 9 hours of incubation are required. When the assay has progressed sufficiently, the supernatant from each well is removed and counted in a scintillation counter. The background counts (determined by the counts in the wells with no enzyme) are subtracted from each sample and the % release calculated in relation to the wells with enzyme only and no inhibitor. The triplicate values for each point are averaged and the data graphed as percent release versus drug concentration. IC$_{50}$'s are determined from the point at which 50% inhibition of release of radiolabeled collagen is obtained.

To determine the identity of the active collagenases in cartilage conditioned medium, assays were carried out using collagen as a substrate, cartilage conditioned medium containing collagenase activity and inhibitors of varying selectivity. The cartilage conditioned medium was collected during the time at which collagen degradation was occurring and thus is representative of the collagenases responsible for the collagen breakdown. Assays were carried out as outlined above except that instead of using recombinant MMP-13 or recombinant MMP-1, cartilage conditioned medium was the enzyme source.

IL-1 Induced Cartilage Collagen Degradation From Bovine Nasal Cartilage

This assay uses bovine nasal cartilage explants which are commonly used to test the efficacy of various compounds to inhibit either IL-1 induced proteoglycan degradation or IL-1 induced collagen degradation. Bovine nasal cartilage is a tissue that is very similar to articular cartilage, i.e. chondrocytes surrounded by a matrix that is primarily type II collagen and aggrecan. The tissue is used because it: (1) is very similar to articular cartilage, (2) is readily available, (3) is relatively homogeneous, and (4) degrades with predictable kinetics after IL-1 stimulation.

Two variations of this assay have been used to assay compounds. Both variations give similar data. The two variations are described below:

Variation 1

Three plugs of bovine nasal cartilage (approximately 2 mm diameter×1.5 mm long) are placed into each well of a 24 well tissue culture plate. One ml of serumless medium is then added to each well. Compounds are prepared as 10 mM stock solutions in DMSO and then diluted appropriately in serumless medium to final concentrations, e.g., 50, 500 and 5000 nM. Each concentration is assayed in triplicate.

Human recombinant IL-1α (5ng/mL) (IL-1) is added to triplicate control wells and to each well containing drug. Triplicate control wells are also set up in which neither drug nor IL-1 are added. The medium is removed and fresh medium containing IL-1 and the appropriate drug concentrations is added on days 6, 12, 18 and 24 or every 3–4 days if necessary. The media removed at each time point is stored at −20° C. for later analysis. When the cartilage in the IL-1 alone wells has almost completely resorbed (about day 21), the experiment is terminated. The medium, is removed and stored. Aliquots (100 μl) from each well at each time point are pooled, digested with papain and then analyzed for hydroxyproline content. Background hydroxyproline (average of wells with no IL-1 and no drug) is subtracted from each data point and the average calculated for each triplicate. The data is then expressed as a percent of the IL-1 alone average value and plotted. The $IC_{50}$ is determined from this plot.

Variation 2

The experimental set-up is the same as outlined above in Variation 1, until day 12. On day 12, the conditioned medium from each well is removed and frozen. Then one ml of phosphate buffered saline (PBS) containing 0.5 μg/ml trypsin is added to each well and incubation continued for a further 48 hours at 37° C. After 48 hours incubation in trypsin, the PBS solution is removed. Aliquots (50 μl) of the PBS/trypsin solution and the previous two time points (days 6 and 12) are pooled, hydrolyzed and hydroxyproline content determined. Background hydroxyproline (average of wells with no IL-1 and no drug) is subtracted from each data point and the average calculated for each triplicate. The data is then expressed as a percent of the IL-1 alone average value and plotted. The $IC_{50}$ is determined from this plot. In this variation, the time course of the experiment is shortened considerably. The addition of trypsin for 48 hours after 12 days of IL-1 stimulation likely releases any type II collagen that has been damaged by collagenase activity but not yet released from the cartilage matrix. In the absence of IL-1 stimulation, trypsin treatment produces only low background levels of collagen degradation in the cartilage explants.

Inhibition of Human 92 kD Gelatinase (MMP-9)

Inhibition of 92 kD gelatinase (MMP-9) activity is assayed using the Mca-Pro-Leu-Gly-Leu-Dpa-Ala-Arg-$NH_2$ substrate (10 μM) under similar conditions as described above for the inhibition of human collagenase (MMP-1).

Human recombinant 92 kD gelatinase (MMP-9, gelatinase B) is activated for 2 hours with 1 mM p-aminophenyl-mercuric acetate (from a freshly prepared 100 mM stock in 0.2 N NaOH) at 37° C.

10 mM dimethylsulfoxide stock solutions of inhibitors are diluted serially in assay buffer (50 mM TRIS, pH 7.5, 200 mM NaCl, 5 mM $CaCl_2$, 20 μM $ZnCl_2$, 0.02% BRIJ-35 (vol./vol.)) using the following scheme:

10 mM→120 μM→12 μM→1.2 μM→0.12 μM

Further dilutions are made as necessary following this same scheme. A minimum of four inhibitor concentrations for each compound are performed in each assay. 25 μL of each concentration is then added to triplicate wells of a black 96 well U-bottomed microfluor plate. As the final assay volume is 100 μL, final concentrations of inhibitor are the result of a further 1:4 dilution (i.e. 30 μM→3 μM→0.3 μM→0.03 μM, etc.). A blank (no enzyme, no inhibitor) and a positive enzyme control (with enzyme, no inhibitor) are also prepared in triplicate.

Activated enzyme is diluted to 100 ng/mL in assay buffer, 25 μL per well is added to appropriate wells of the microplate. Final enzyme concentration in the assay is 25 ng/mL (0.27 nM).

A five mM dimethylsulfoxide stock solution of substrate (Mca-Pro-Leu-Gly-Leu-Dpa-Ala-Arg-$NH_2$) is diluted in assay buffer to 20 μM. The assay is initiated by addition of 50 μL of diluted substrate yielding a final assay concentration of 10 μM substrate. A zero time fluorescence reading (320 excitation; 390 emission) is immediately taken and subsequent readings are taken every fifteen minutes at room temperature with a PerSeptive Biosystems CytoFluor Multi-Well Plate Reader with the gain at 90 units.

The average value of fluorescence of the enzyme and blank are plotted versus time. An early time point on the linear part of this curve is chosen for $IC_{50}$ determinations. The zero time point for each compound at each dilution is subtracted from the latter time point and the data then expressed as percent of enzyme control (inhibitor fluorescence divided by fluorescence of positive enzyme control ×100). Data is plotted as inhibitor concentration versus percent of enzyme control. $IC_{50}$'s are defined as the concentration of inhibitor that gives a signal that is 50% of the positive enzyme control.

Aggrecanase Assay

Primary porcine chondrocytes from articular joint cartilage are isolated by sequential trypsin and collagenase digestion followed by collagenase digestion overnight and are plated at $2 \times 10^5$ cells per well into 48 well plates with 5 μCi/ml 35 S (1000 Ci/mmol) sulphur in type I collagen coated plates. Cells are allowed to incorporate label into their proteoglycan matrix (approximately 1 week) at 37° C., under an atmosphere of 5% $CO_2$.

The night before initiating the assay, chondrocyte monolayers are washed two times in DMEM/1% PSF/G and then allowed to incubate in fresh DMEM/1% FBS overnight.

The following morning chondrocytes are washed once in DMEM/1% PSF/G. The final wash is allowed to sit on the plates in the incubator while making dilutions.

Media and dilutions can be made as described in the Table below.

| | |
|---|---|
| Control Media | DMEM alone (control media) |
| IL-1 Media | DMEM + IL-1 (5 ng/ml) |
| Drug Dilutions | Make all compounds stocks at 10 mM in DMSO. Make a 100 μM stock of each compound in DMEM in 96 well plate. Store in freezer overnight. The next day perform serial dilutions in DMEM with IL-1 to 5 μM, 500 nM, and 50 nM. Aspirate final wash from wells and add 50 μl of compound from above dilutions to 450 μl of IL-1 media in appropriate wells of the 48 well plates. Final compound concentrations equal 500 nM, 50 nM, and 5 nM. All samples completed in triplicate with Control and IL-1 alone samples on each plate. |

Plates are labeled and only the interior 24 wells of the plate are used. On one of the plates, several columns are designated as IL-1 (no drug) and Control (no IL-1, no drug). These control columns are periodically counted to monitor 35S-proteoglycan release. Control and IL-1 media are added to wells (450 μl) followed by compound (50 μl) so as to initiate the assay. Plates are incubated at 37° C., with a 5% $CO_2$ atmosphere.

At 40–50% release (when CPM from IL-1 media is 4–5 times control media) as assessed by liquid scintillation counting (LSC) of media samples, the assay is terminated (9–12 hours). Media is removed from all wells and placed in scintillation tubes. Scintillate is added and radioactive counts are acquired (LSC). To solubilize cell layers, 500 μl of papain digestion buffer (0.2 M Tris, pH 7.0, 5 mM EDTA, 5 mM DTT, and 1 mg/ml papain) is added to each well.

Plates with digestion solution are incubated at 60° C. overnight. The cell layer is removed from the plates the next day and placed in scintillation tubes. Scintillate is then added, and samples counted (LSC).

The percent of released counts from the total present in each well is determined. Averages of the triplicates are made with control background subtracted from each well. The percent of compound inhibition is based on IL-1 samples as 0% inhibition (100% of total counts).

Inhibition of Soluble TNF Production

The ability of the compounds or the pharmaceutically acceptable salts thereof to inhibit the cellular production/release of TNF and, consequently, demonstrate their effectiveness for treating diseases involving the dysregulated of TNF is shown by the following in vitro assay:

Method for the Evaluation of Recombinant TNFα Converting Enzyme Activity

Preparation of Recombinant TACE

A DNA fragment coding for the signal sequence, pro-domain and catalytic domain of TACE (amino acids 1–473), was amplified by polymerase chain reaction using a human lung cDNA library as a template. The amplified fragment was cloned into pFastBac vector. The DNA sequence of the insert was confirmed for both the strands. A bacmid prepared using pFastBac in $E.\ coli$ DH10Bac was transfected into SF9 insect cells. The virus particles were amplified to P1, P2, P3 stages. The P3 virus was infected into both Sf9 and High Five insect cells and grown at 27° C. for 48 hours. The medium was collected and used for assays and further purification.

Preparation of Fluorescent Quenched Substrate

A model peptidic TNF-α substrate (LY-LeucineAlanineGlutamineAlanineValineArginineSerine SerineLysine(CMTR)-Arginine (LY=Lucifer Yellow; CMTR=5-carboxytetramethyl Rhodamine)) was prepared and the concentration estimated by absorbance at 560 nm (E560, 60,000 M-1CM-1) according to the method of Geoghegan, K F, "Improved method for converting an unmodified peptide to an energy-transfer substrate for a proteinase." $Bioconjugate\ Chem.$ 7, 385–391 (1995). This peptide encompasses the cleavage cite on pro-TNF which is cleaved in vivo by TACE.

Enzyme Reaction

The reaction, carried out in a 96 well plate (Dynatech), was comprised of 70 μl of buffer solution (25 mM Hepes-HCl, pH7.5, plus 20 μM $ZnCl_2$), 10 μl of 100 μM fluorescent quenched substrate, 10 μl of a DMSO (5%) solution of test compound, and an amount of r-TACE enzyme which will cause 50% cleavage in 60 minutes—in a total volume of 100 μl. The specificity of the enzyme cleavage at the amide bond between alanine and valine was verified by HPLC and mass spectrometry. Initial rates of cleavage were monitored by measuring the rate of increase in fluorescence at 530 nm (excitation at 409 nm) over 30 minutes. The experiment was controlled as follows: 1) for background fluorescence of substrate; 2) for fluorescence of fully cleaved substrate; 3) for fluorescence quenching or augmentation from solutions containing test compound.

Data was analyzed as follows. The rates from the non-test compound containing "control" reactions were averaged to establish the 100% value. The rate of reaction in the presence of test compound was compared to that in the absence of compound, and tabulated as "percent of non-test compound containing control. The results were plotted as "% of control" vs. the log of compound concentration and a half-maximal point or $IC_{50}$ value determined. The $IC_{50}$ for the above assay is a measure of the inhibition of the TNF-α proteolytic activity of TACE. Blockage of binding of TNF-α to TACE as used herein is as described in U.S. Pat. No. 5,830,742, issued Nov. 3, 1998.

Monocyte Assay

Human mononuclear cells were isolated from anti-coagulated human blood using a one-step Ficoll-hypaque separation technique. (2) The mononuclear cells were washed three times in Hanks balanced salt solution (HBSS) with divalent cations and resuspended to a density of $2\times10^6$/ml in HBSS containing 1% BSA. Differential counts determined using the Abbott Cell Dyn 3500 analyzer indicated that monocytes ranged from 17 to 24% of the total cells in these preparations.

180 m of the cell suspension was aliquoted into flat bottom 96 well plates (Costar). Additions of compounds and LPS (100 ng/ml final concentration) gave a final volume of 200 μl. All conditions were performed in triplicate. After a four hour incubation at 37° C. in an humidified $CO_2$ incubator, plates were removed and centrifuged (10 minutes at approximately 250×g) and the supernatants removed and assayed for TNF-α using the R&D ELISA Kit.

A group of preferred compounds, more preferably compounds of the formula (I), that can be identified by the methods of the present invention include those inhibitors that possess potent activity against MMP-2 and MMP-9 (preferably an $IC_{50}$ of less than 500 nM, more preferably 100 nM, most preferably 50 nM) preferably wherein said MMP-2 and MMP-9 inhibitory activity is selective activity for MMP-2 and MMP-9. The compounds of formula (I) possess surprisingly selective activity against MMP-2 and MMP-9. Specifically, compounds of formula (I) have $IC_{50}$'s of less than 500 nM against either or both of MMP-2 and MMP-9.

For administration to mammals, including humans, in accordance with the methods of treatment of the present invention, for the treatment of a disorder, conditions or disease of the peripheral or central nervous system, a variety of conventional routes may be used including oral, parenteral (e.g., intravenous, intramuscular or subcutaneous), buccal, anal and topical. In general, the compounds of the invention (hereinafter also known as the active compounds) will be administered at dosages between about 0.1 and 25 mg/kg body weight of the subject to be treated per day, preferably from about 0.3 to 5 mg/kg. Preferably the active compound will be administered orally or parenterally. However, some variation in dosage will necessarily occur depending on the condition of the subject being treated. The person responsible for administration will, in any event, determine the appropriate dose for the individual subject.

The compounds of the present invention can be administered in a wide variety of different dosage forms, in general, the therapeutically effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelation and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof. In the case of animals, they are advantageously contained in an animal feed or drinking water in a concentration of 5–5000 ppm, preferably 25 to 500 ppm.

For parenteral administration (intramuscular, intraperitoneal, subcutaneous and intravenous use) in accordance with the present invention, a sterile injectable solution of the active ingredient is usually prepared. Solutions of a therapeutic compound of the present invention in either sesame or peanut oil or in aqueous propylene glycol may be employed. The aqueous solutions should be suitably adjusted and buffered, preferably at a pH of greater than 8, if necessary and the liquid diluent first rendered isotonic. These aqueous solutions are suitable intravenous injection purposes. The oily solutions are suitable for intraarticular, intramuscular and. subcutaneous injection purposes. The preparation of all these solutions under sterile conditions is readily accomplished by standard pharmaceutical techniques well known to those skilled in the art. In the case of animals, compounds can be administered intramuscularly or subcutaneously at dosage levels of about 0.1 to 50 mg/kg/day, advantageously 0.2 to 10 mg/kg/day given in a single dose or up to 3 divided doses.

For the methods of the present invention, the active compounds herein disclosed may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

What is claimed is:

1. A method of treating in a mammal a disease, condition or disorder characterized by MMP-2 or MMP-9 activity and selected from the group consisting of: Alzheimer's disease, stroke/cerebral ischemia, head trauma, spinal cord injury, amyotrophic lateral sclerosis, Huntington's disease, Parkinson's disease, migraine, cerebral amyloid angiopathy, age-related cognitive decline; mild cognitive impairment and prion diseases, comprising the administration to said mammal a therapeutically effective amount of a compound of formula (I):

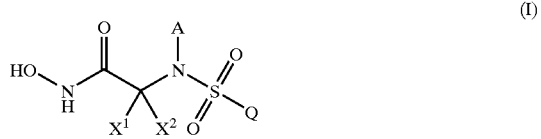

or the pharmaceutically acceptable salts thereof, wherein

A is H or —$(CH_2)_n$—(C=O)—Z; where n is 1 to 6; and Z is hydroxy, $(C_1-C_6)$alkoxy or $NR^1R^2$ wherein $R^1$ and $R^2$ are each independently selected from the group consisting of hydrogen, $(C_1-C_6)$alkyl, piperidyl, $(C_1-C_6)$alkylpiperidyl, $(C_6-C_{10})$arylpiperidyl, $(C_2-C_9)$heteroarylpiperidyl, $(C_6-C_{10})$aryl$(C_1-C_6)$alkylpiperidyl, $(C_2-C_9)$heteroaryl$(C_1-C_6)$alkylpiperidyl, $(C_1-C_6)$acylpiperidyl, $(C_6-C_{10})$aryl, $(C_2-C_9)$heteroaryl, $(C_6-C_{10})$aryl$(C_1-C_6)$alkyl, $(C_2-C_9)$heteroaryl$(C_1-C_6)$alkyl, $(C_6-C_{10})$aryl$(C_6-C_{10})$aryl$(C_6-C_{10})$aryl$(C_1-C_6)$alkyl, $(C_3-C_6)$cycloalkyl, $(C_3-C_6)$cycloalkyl$(C_1-C_6)$alkyl, $R^5(C_2-C_6)$alkyl, $(C_1-C_5)$alkyl$(CHR^3)(C_1-C_6)$alkyl wherein $R^3$ is hydroxy, $(C_1-C_6)$acyloxy, $(C_1-C_6)$alkoxy, piperazino, $(C_1-C_6)$acylamino, $(C_1-C_6)$alkylthio, $(C_6-C_{10})$arylthio, $(C_1-C_6)$alkylsulfinyl, $(C_6-C_{10})$arylsulfinyl, $(C_1-C_6)$alkylsulfoxyl, $(C_6-C_{10})$arylsulfoxyl, amino, $(C_1-C_6)$alkylamino, $((C_1-C_6)$alkyl$)_2$ amino, $(C_1-C_6)$acylpiperazino, $(C_1-C_6)$alkylpiperazino, $(C_6-C_{10})$aryl$(C_1-C_6)$alkylpiperazino, $(C_2-C_9)$heteroaryl$(C_1-C_6)$alkylpiperazino, morpholino, thiomorpholino, piperidino or pyrrolidino; $R^4(C_1-C_6)$alkyl, $(C_1-C_5)$alkyl$(CHR^4)(C_1-C_6)$alkyl wherein $R^4$ is piperidyl, $(C_1-C_6)$alkylpiperidyl, $(C_6-C_{10})$arylpiperidyl, $(C_6-C_{10})$aryl$(C_1-C_6)$alkylpiperidyl, $(C_2-C_9)$heteroarylpiperidyl or $(C_2-C_9)$heteroaryl$(C_1-C_6)$alkylpiperidyl; and $CH(R^5)COR^6$ wherein $R^5$ is hydrogen, $(C_1-C_6)$alkyl, $(C_6-C_{10})$aryl$(C_1-C_6)$alkyl, $(C_2-C_9)$heteroaryl$(C_1-C_6)$alkyl, $(C_1-C_6)$alkylthio $(C_1-C_6)$alkyl, $(C_6-C_{10})$arylthio$(C_1-C_6)$alkyl, $(C_1-C_6)$alkylsulfinyl$(C_1-C_{10})$arylsulfinyl$(C_1-C_6)$alkyl, $(C_1-C_6)$alkylsulfonyl$(C_1-C_6)$alkyl, $(C_6-C_{10})$arylsulfonyl$(C_1-C_6)$alkyl, hydroxy$(C_1-C_6)$alkyl, amino$(C_1-C_6)$alkyl, $(C_1-C_6)$alkylamino$(C_1-C_6)$alkyl, $((C_1-C_6)$alkylamino$)_2(C_1-C_6)_2(C_1-C_6)$alkyl, $R^7R^8NCO(C_1-C_6)$alkyl or $R7OCO(C_1-C_6)$alkyl wherein $R^7$ and $R^8$ are each independently selected from the group consisting of hydrogen, $(C_1-C_6)$alkyl, $(C_6-C_{10})$aryl$(C_1-C_6)$alkyl and $(C_2-C_9)$heteroaryl $(C_1-C_6)$alkyl; and $R^6$ is $R^9O$ or $R^9R^{10}N$ wherein $R^9$ and $R^{10}$ are each independently selected from the group consisting of hydrogen, $(C_1-C_6)$alkyl, $(C_6-C_{10})$aryl $(C_1-C_6)$alkyl and $(C_2-C_9)$heteroaryl$(C_1-C_6)$alkyl;

or $R^1$ and $R^2$, or $R^7$ and $R^8$, or $R^9$ and $R^{10}$ may be taken together to form an azetidinyl, pyrrolidinyl, morpholinyl, thiomorpholinyl, indolinyl, isoindolinyl, tetrahydroquinolinyl, tetrahydroisoquinolinyl, $(C_1-C_6)$ acylpiperazinyl, $(C_1-C_6)$alkylpiperazinyl, $(C_6-C_{10})$ arylpiperazinyl, $(C_2-C_9)$heteroarylpiperazinyl or a bridged diazabicycloalkyl ring selected from the group consisting of:

(J₁)

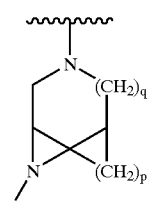

(J₂)

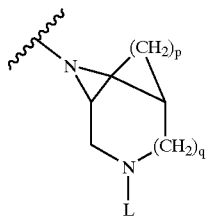

(J₃)

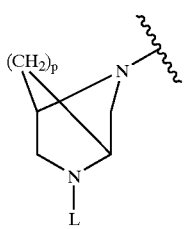

(J₄)

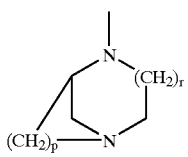

and (J₅)

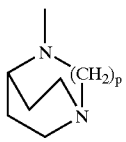

wherein p is 1, 2 or 3;
q is 1 or 2;
r is 0 or 1;
L is hydrogen, $(C_1-C_3)$alkyl or $(C_1-C_6)$acyl;
$X^1$ and $X^2$ are each independently selected from the group consisting of hydrogen, $(C_1-C_6)$alkyl, trifluoromethyl, trifluoromethyl$(C_1-C_6)$alkyl, $(C_1-C_6)$alkyl (difluoromethylene), $(C_1-C_3)$alkyl(difluoromethylene) $(C_1-C_3)$alkyl, $(C_6-C_{10})$aryl, $(C_2-C_9)$heteroaryl, $(C_6-C_{10})$aryl$(C_1-C_6)$alkyl, $(C_2-C_9)$heteroaryl$(C_1-C_6)$alkyl, $(C_6-C_{10})$aryl$(C_6-C_{10})$aryl, $(C_6-C_{10})$aryl $(C_6-C_{10})$aryl$(C_1-C_6)$alkyl, $(C_3-C_6)$cycloalkyl, $(C_3-C_6)$cycloalkyl$(C_1-C_6)$alkyl, hydroxy$(C_1-C_6)$alkyl, $(C_1-C_6)$acyloxy$(C_1-C_6)$alkyl, piperazinyl $(C_1-C_6)$alkyl, $(C_1-C_6)$acylamino$(C_1-C_6)$alkyl, piperidyl, $(C_1-C_6)$alkylpiperidyl, $(C_6-C_{10})$aryl$(C_1-C_6)$ alkoxy$(C_1-C_6)$alkyl, $(C_2-C_9)$heteroaryl$(C_1-C_6)$alkoxy $(C_1-C_6)$alkyl, $(C_1-C_6)$alkylthio$(C_1-C_6)$alkyl, $(C_6-C_{10})$ arylthio$(C_1-C_6)$alkyl, $(C_1-C_6)$alkylsulfinyl$(C_1-C_6)$ alkyl, $(C_6-C_{10})$arylsulfinyl$(C_1-C_6)$alkyl, $(C_1-C_6)$ alkylsulfonyl$(C_1-C_6)$alkyl, $(C_6-C_{10})$arylsulfonyl $(C_1-C_6)$alkyl, amino$(C_1-C_6)$alkyl, $(C_1-C_6)$alkylamino $(C_1-C_6)$alkyl, $((C_1-C_6)$alkylamino$)_2(C_1-C_6)$alkyl, $R^{11}CO(C_1-C_6)$alkyl wherein $R^{11}$ is $R^{12}O$ or $R^{12}R^{13}N$ wherein $R^{12}$ and $R^{13}$ are each independently selected from the group consisting of hydrogen, $(C_1-C_6)$alkyl, $(C_6-C_{10})$aryl$(C_1-C_6)$alkyl or $(C_2-C_9)$heteroaryl $(C_1-C_6)$alkyl; and $R^{14}(C_1-C_6)$alkyl wherein $R^{14}$ is $(C_1-C_6)$acylpiperazino, $(C_6-C_{10})$arylpiperazino, $(C_2-C_9)$heteroarylpiperazino, $(C_1-C_6)$alkylpiperazino, $(C_6-C_{10})$aryl$(C_1-C_6)$alkylpiperazino, $(C_2-C_9)$ heteroaryl$(C_1-C_6)$alkylpiperazino, morpholino, thiomorpholino, piperidino, pyrrolidino, piperidyl, $(C_1-C_6)$alkylpiperidyl, $(C_6-C_{10})$arylpiperidyl, $(C_2-C_9)$ heteroarylpiperidyl, $(C_6-C_{10})$aryl$(C_1-C_6)$ alkylpiperidyl, $(C_2-C_9)$heteroaryl$(C_1-C_6)$ alkylpiperidyl or $(C_1-C_6)$acylpiperidyl;

or $X^1$ and $X^2$ may be taken together to form a $(C_3-C_6)$ cycloalkyl, a benzo-fused $(C_3-C_6)$cycloalkyl ring or a group of the formula $(J_7)$:

(J₇)

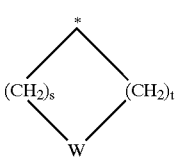

wherein the carbon atom bearing the asterisk is the carbon to which $X^1$ and $X^2$ are attached, s and t are independently 1 or 2, and W is $CF_2$, O, S, $SO_2$ or $NR^{15}$, wherein $R^{15}$ is hydrogen, $(C_1-C_6)$alkyl, $(C_6-C_{10})$acyl, $(C_6-C_{10})$aryl, $(C_2-C_9)$heteroaryl, $(C_6-C_{10})$aryl$(C_1-C_6)$ alkyl, $(C_2-C_9)$heteroaryl$(C_1-C_6)$alkyl, $(C_1-C_6)$ alkylsulfonyl, $(C_6-C_{10})$arylsulfonyl or $(C_1-C_6)$alkyl (C=O)—;

Q is $(C_1-C_6)$alkyl, $(C_6-C_{10})$aryl, $(C_6-C_{10})$aryloxy $(C_6-C_{10})$aryl, $(C_6-C_{10})$aryl$(C_6-C_{10})$aryl, $(C_6-C_{10})$aryl $(C_6-C_{10})$aryl$(C_1-C_6)$alkyl, $(C_6-C_{10})$aryl$(C_2-C_9)$ heteroaryl, $(C_6-C_{10})$aryloxy$(C_2-C_9)$heteroaryl, $(C_2-C_9)$heteroaryl$(C_2-C_9)$heteroaryl, $(C_2-C_9)$heteroaryl$(C_6-C_{10})$aryl, $(C_1-C_6)$ alkyl$(C_6-C_{10})$aryl, $(C_1-C_6)$alkoxy$(C_6-C_{10})$aryl, $((C_1-C_6)$alkoxy$)_2(C_6-C_{10})$aryl, $(C_6-C_{10})$aryl$(C_1-C_6)$ alkoxy$(C_6-C_{10})$aryl, $(C_6-C_{10})$aryl$(C_1-C_6)$alkoxy $(C_1-C_6)$alkyl, $(C_2-C_9)$heteroaryloxy$(C_6-C_{10})$aryl, $(C_1-C_6)$alkyl$(C_2-C_9)$heteroaryl, $(C_1-C_6)$alkoxy $(C_2-C_9)$heteroaryl, $((C_1-C_6)$alkoxy$)_2(C_2-C_9)$ heteroaryl, $(C_6-C_{10})$aryl$(C_1-C_6)$alkoxy$(C_2-C_9)$ heteroaryl, $(C_2-C_9)$heteroaryloxy$(C_2-C_9)$heteroaryl, $(C_6-C_{10})$aryloxy$(C_1-C_6)$alkyl, $(C_2-C_9)$heteroaryloxy $(C_1-C_6)$alkyl, $(C_1-C_6)$alkyl$(C_6-C_{10})$aryloxy$(C_6-C_{10})$ aryl, $(C_1-C_6)$alkyl$(C_2-C_9)$heteroaryloxy$(C_6-C_{10})$aryl, $(C_1-C_6)$alkyl$(C_6-C_{10})$aryloxy$(C_2-C_9)$heteroaryl, $(C_1-C_6)$alkoxy$(C_6-C_{10})$aryloxy$(C_6-C_{10})$aryl, $(C_1-C_6)$ alkoxy$(C_2-C_9)$heteroaryloxy$(C_6-C_{10})$aryl or $(C_1-C_6)$ alkoxy$(C_6-C_{10})$aryloxy$(C_2-C_9)$heteroaryl, wherein each of the foregoing aryl groups may be optionally substituted by fluoro, chloro, bromo, trifluoromethyl, trifluoromethoxy, difluoromethoxy, $(C_1-C_6)$alkyl, $(C_1-C_6)$alkoxy or perfluoro$(C_1-C_3)$alkyl;

with the proviso that when either $X^1$ or $X^2$ is $CH(R^5)$ $COR^6$ wherein $R^5$ and $R^6$ are as defined above, the other of $X^1$ or $X^2$ is hydrogen, $(C_1-C_6)$alkyl or benzyl.

2. A method of treatment according to claim 1, wherein A is —(CH₂)ₙ—(C=O)—Z.

3. A method of treatment according to claim 2, wherein n is 2.

4. A method of treatment according to claim 2, wherein Q is 4-methoxyphenyl or 4-phenoxyphenyl, optionally substituted by fluoro, chloro, bromo, trifluoromethyl, trifluoromethoxy, difluoromethoxy, $(C_1-C_6)$alkyl, $(C_1-C_6)$ alkoxy or perfluoro$(C_1-C_3)$alkyl.

5. A method of treatment according to claim 2, wherein Z is hydroxy, Q is 4-methoxyphenyl or 4-phenoxyphenyl, optionally substituted by fluoro, chloro, bromo, trifluoromethyl, trifluoromethoxy, difluoromethoxy, $(C_1-C_6)$ alkyl, $(C_1-C_6)$alkoxy or perfluoro$(C_1-C_3)$alkyl, and either $X^1$ or $X^2$ is not hydrogen.

6. A method of treatment according to claim 2, wherein Q is 4-methoxyphenyl or 4-phenoxyphenyl, , optionally substituted by fluoro, chloro, bromo, trifluoromethyl, trifluoromethoxy, difluoromethoxy, $(C_1-C_6)$alkyl, $(C_1-C_6)$ alkoxy or perfluoro$(C_1-C_3)$alkyl, and $X^1$ and $X^2$ are taken together to form $(C_3-C_6)$cycloalkyl, oxacyclohexanyl, thiocyclohexanyl, indanyl or a group of the formula

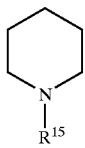

wherein $R^{15}$ is $(C_1-C_6)$acyl, $(C_1-C_6)$alkyl, $(C_6-C_{10})$aryl $(C_1-C_6)$alkyl, $(C_2-C_9)$heteroaryl$(C_1-C_6)$alkyl or $(C_1-C_6)$ alkylsulfonyl.

7. A method of treatment according to claim 1, comprising the administration of a compound of the formula (Ic):

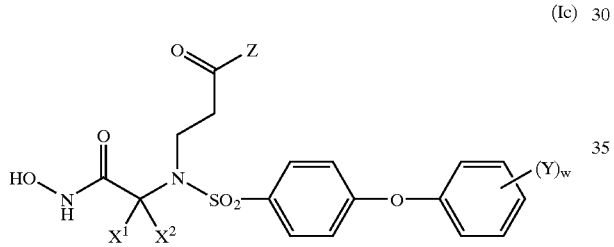

or the pharmaceutically acceptable salts thereof, wherein
$X^1$ is $(C_1-C_6)$alkyl;
$X^2$ is $(C_1-C_6)$alkyl; or
$X^1$ and $X^2$ taken together with the carbon atom to which they are attached form a ring selected from $(C_5-C_7)$ cycloalkyl, 4-tetrahydropyranyl and 4-piperidinyl;
Z is hydroxy or $(C_1-C_6)$alkoxy;
each Y is independently selected from hydrogen, fluoro, chloro, trifluoromethyl, $(C_1-C_6)$alkoxy, trifluoromethoxy, difluoromethoxy and $(C_1-C_6)$alkyl; and w is 1 or 2.

8. A method of treatment according to claim 7, wherein Y is fluoro or chloro.

9. A method of treatment according to claim 7, wherein Y is fluoro or chloro at the 4-position of the phenoxy ring.

10. A method of treatment according to claim 7, wherein $X^1$ and $X^2$ taken together with the carbon atom to which they are attached form a cyclopentyl or 4-tetrahydropyranyl ring.

11. A method of treatment according to claim 7, wherein Z is hydroxy.

12. A method of treatment according to claim 7, comprising the administration of a compound selected from the group consisting of:

3-[[4-(4-fluorophenoxy)benzenesulfonyl]-(1-hydroxycarbamoylcyclopentyl) amino]-propionic acid ethyl ester;

3-[[4-(4-fluorophenoxy)benzenesulfonyl]-(1-hydroxycarbamoylcyclopentyl) amino]propionic acid;

3-[[4-(4-fluorophenoxy)benzenesulfonyl]-(1-hydroxycarbamoyl-1-methylethyl) amino]propionic acid ethyl ester;

3-[[4-(4-fluorophenoxy)benzenesulfonyl]-(1-hydroxycarbamoyl-1-methylethyl) amino]propionic acid;

3-[[$^4$-(4-fluorophenoxy)benzenesulfonyl]-(4-hydroxycarbamoyltetrahydro-pyran4-yl)-amino] propionic acid;

3-[[4-(4-fluorophenoxy)benzenesulfonyl]-(4-hydroxycarbamoyltetrahydro-pyran-4-yl)-amino] propionic acid ethyl ester;

3-[[4-(4-chlorophenoxy)benzenesulfonyl]-(4-hydroxycarbamoyltetrahydro-pyran4-yl)-amino] propionic acid;

3-[[4-(4-chlorophenoxy)benzenesulfonyl]-(4-hydroxycarbamoyltetrahydro-pyran-4-yl)-amino] propionic acid ethyl ester;

3-[(4-hydroxycarbamoyltetrahydropyran-4-yl)-(4-phenoxybenzenesulfonyl) amino]-propionic acid;

3-[($^4$-hydroxycarbamoyltetrahydropyran4-yl)-(4-phenoxybenzenesulfonyl) amino]-propionic acid ethyl ester;

3-[[4-(4-fluorophenoxy)benzenesulfonyl]-(4-hydroxycarbamoylpiperidin4-yl)-amino]propionic acid ethyl ester;

3-[[4-(4-chlorophenoxy)benzenesulfonyl]-(1-hydroxycarbamoyl-1-methylethyl) amino]-propionic acid;

3-[[4-(4-chlorophenoxy)benzenesulfonyl]-(1-hydroxycarbamoyl-1-methylethyl) amino]-propionic acid ethyl ester;

3-[[4-(4-fluorophenoxy)benzenesulfonyl]-(1-hydroxycarbamoylcyclohexyl) amino]-propionic acid;

3-[(1-hydroxycarbamoylcyclopentyl)-(4-phenoxybenzenesulfonyl) amino]propionic acid;

3-[[4-(4-chlorophenoxy)benzenesulfonyl]-(1-hydroxycarbamoylcyclopentyl) amino]-propionic acid and pharmaceutically acceptable salts thereof.

* * * * *